(12) United States Patent
Okubo et al.

(10) Patent No.: US 10,161,950 B2
(45) Date of Patent: Dec. 25, 2018

(54) REAGENT PREPARING DEVICE, REAGENT PREPARING METHOD, AND SPECIMEN PROCESSING SYSTEM

(75) Inventors: Koichi Okubo, Kobe (JP); Noriyuki Nakanishi, Kakogawa (JP); Masahiko Oguro, Kobe (JP); Tomoyuki Asahara, Kobe (JP); Takayuki Nakajima, Nishinomiya (JP)

(73) Assignee: Sysmex Corporation, Kobe-Shi, Hyogo (JP)

( * ) Notice: Subject to any disclaimer, the term of this patent is extended or adjusted under 35 U.S.C. 154(b) by 506 days.

(21) Appl. No.: 12/748,768

(22) Filed: Mar. 29, 2010

(65) Prior Publication Data
US 2010/0248208 A1  Sep. 30, 2010

(30) Foreign Application Priority Data
Mar. 31, 2009 (JP) ................................. 2009-084488

(51) Int. Cl.
| | | |
|---|---|---|
| *C12Q 1/02* | (2006.01) | |
| *C12M 1/34* | (2006.01) | |
| *G01N 35/10* | (2006.01) | |
| *G01N 35/00* | (2006.01) | |

(52) U.S. Cl.
CPC ... *G01N 35/1002* (2013.01); *G01N 35/00663* (2013.01)

(58) Field of Classification Search
CPC ...................... G01N 35/1002; G01N 35/00663
See application file for complete search history.

(56) References Cited

U.S. PATENT DOCUMENTS

| | | | | |
|---|---|---|---|---|
| 3,952,509 A | * | 4/1976 | Coleman ......................... | 60/422 |
| 4,711,089 A | * | 12/1987 | Archung ......................... | 60/405 |
| 4,980,130 A | * | 12/1990 | Metzger .................... | G01N 1/28 |
| | | | | 422/510 |
| 5,158,748 A | * | 10/1992 | Obi et al. ...................... | 422/511 |
| 5,389,339 A | * | 2/1995 | Petschek et al. ............... | 422/64 |
| 5,800,056 A | * | 9/1998 | Suzuki et al. ............. | 366/152.4 |
| 7,169,362 B2 | * | 1/2007 | Toi et al. ...................... | 422/511 |
| 2001/0042413 A1 | * | 11/2001 | Sakairi et al. ............. | 73/863.11 |

(Continued)

FOREIGN PATENT DOCUMENTS

| | | |
|---|---|---|
| JP | 64-58340 A | 3/1989 |
| JP | 11-271309 A | 10/1999 |

(Continued)

*Primary Examiner* — Benjamin R Whatley
(74) *Attorney, Agent, or Firm* — Brinks Gilson & Lione

(57) ABSTRACT

A reagent preparing device capable of supplying a predetermined reagent, which includes a first liquid and a second liquid different from the first liquid, to a measurement section for measuring a specimen using the reagent, comprising: a pressure generator for generating pressure to transfer liquid; a reagent preparing section for executing a preparation operation of the predetermined reagent using the pressure generated by the pressure generator; and a controller configured for performing operations comprising: determining whether or not the reagent preparing section is executing the preparation operation, and controlling the generation of the pressure by the pressure generator according to the determination result, is disclosed. A reagent preparing method and a specimen processing system are also disclosed.

7 Claims, 13 Drawing Sheets

(56) References Cited

U.S. PATENT DOCUMENTS

| | | | |
|---|---|---|---|
| 2001/0047692 A1* | 12/2001 | Lipscomb et al. | 73/864.25 |
| 2002/0016568 A1* | 2/2002 | Lebel et al. | 604/131 |
| 2004/0023404 A1* | 2/2004 | Shibata | 436/155 |
| 2004/0260514 A1* | 12/2004 | Beaudoin et al. | 702/182 |
| 2005/0121338 A1* | 6/2005 | Inoue | 205/775 |
| 2007/0212261 A1* | 9/2007 | Tanaka et al. | 422/67 |
| 2008/0237142 A1* | 10/2008 | Carpenter et al. | 210/741 |
| 2008/0264179 A1* | 10/2008 | Dee et al. | 73/851 |
| 2009/0139399 A1* | 6/2009 | Kang et al. | 95/24 |
| 2010/0161243 A1* | 6/2010 | Nagai et al. | 702/25 |
| 2010/0216224 A1* | 8/2010 | Okubo | G01N 1/38 435/286.5 |
| 2010/0248289 A1* | 9/2010 | Asahara | G01N 35/00663 435/29 |
| 2011/0045498 A1* | 2/2011 | Lindberg | G01N 35/00029 435/7.21 |

FOREIGN PATENT DOCUMENTS

| | | | | |
|---|---|---|---|---|
| JP | 11-348379 A | 12/1999 | | |
| JP | 2001-235408 A | 8/2001 | | |
| JP | 2007-240430 A | 9/2007 | | |
| WO | WO 2009/031461 A1 | 3/2009 | | |
| WO | WO 2009026919 A2 * | 3/2009 | | G01N 35/00029 |

* cited by examiner

REAGENT PREPARING DEVICE, REAGENT PREPARING METHOD, AND SPECIMEN PROCESSING SYSTEM

RELATED APPLICATIONS

This application claims priority under 35 U.S.C. § 119 to Japanese Patent Application No. 2009-084488 filed on Mar. 31, 2009, the entire content of which is hereby incorporated by reference.

BACKGROUND OF THE INVENTION

1. Field of the Invention

The present invention relates to reagent preparing devices, reagent preparing methods, and specimen processing systems, and in particular, to a reagent preparing device, a reagent preparing method, and a specimen processing system capable of preparing the reagent to use in the measurement of the specimen.

2. Description of the Related Art

A reagent preparing device capable of preparing the reagent to use in the measurement of the specimen is conventionally known (see e.g., U.S. Pat. No. 5,800,056).

U.S. Pat. No. 5,800,056 discloses a reagent preparing device including a reagent quantifying tank for accommodating a high concentration reagent, a pure water quantifying tank for accommodating pure water, and a preparing tank for preparing the reagent when the high concentration reagent is transferred from the reagent quantifying tank and the pure water is transferred from the pure water quantifying tank. However, U.S. Pat. No. 5,800,056 does not disclose nor suggest the technique of reducing the power consumption.

A technique of reducing the power consumption is known (see e.g., Japanese Laid-Open Patent Publication No. 11-271309). Japanese Laid-Open Patent Publication No. 11-271309 discloses a specimen pre-processing system device including a barcode printer for barcode label attached to a test tube for accommodating the specimen, and a barcode reader for reading the barcode label attached to the test tube. The specimen pre-processing system device turns OFF the power supply when not operating and turns ON the power supply immediately before the operation (one second before operation) and again turns OFF the power supply when the operation is terminated for the barcode printer and the barcode reader. The power consumption of the barcode printer for the barcode label attached to the test tube and the barcode reader used in the specimen pre-processing system device thus can be reduced.

However, Japanese Laid-Open Patent Publication No. 11-271309 merely discloses a technique of reducing the power consumption of the barcode printer for the barcode label attached to the test tube and the barcode reader used in the specimen pre-processing system device, and does not describe reducing the power consumption of a reagent preparing device.

SUMMARY OF THE INVENTION

The scope of the present invention is defined solely by the appended claims, and is not affected to any degree by the statements within this summary.

A first aspect of the present invention is a reagent preparing device capable of supplying a predetermined reagent, which includes a first liquid and a second liquid different from the first liquid, to a measurement section for measuring a specimen using the reagent, comprising: a pressure generator for generating pressure to transfer liquid; a reagent preparing section for executing a preparation operation of the predetermined reagent using the pressure generated by the pressure generator; and a controller configured for performing operations comprising: determining whether or not the reagent preparing section is executing the preparation operation, and controlling the generation of the pressure by the pressure generator according to the determination result.

A second aspect of the present invention is a reagent preparing method of preparing a predetermined reagent, which includes a first liquid and a second liquid different from the first liquid, to be supplied to a measurement section for measuring a specimen using the reagent, comprising: generating pressure to transfer liquid; executing a preparation operation of the predetermined reagent using the generated pressure; determining whether or not the preparation operation is being executed; and controlling the generation of the pressure according to the determination result.

A third aspect of the present invention is a specimen processing system comprising: a measurement section for measuring a specimen using a predetermined reagent, which includes a first liquid and a second liquid different from the first liquid; a pressure generator for generating pressure to transfer liquid; a reagent preparing section for executing a preparation operation of the predetermined reagent using the pressure generated by the pressure generator; and a controller configured for performing operations comprising: determining whether or not the reagent preparing section is executing the preparation operation, and controlling the generation of the pressure by the pressure generator according to the determination result.

DETAILED DESCRIPTION OF THE PREFERRED EMBODIMENTS

The preferred embodiments of the present invention will be described hereinafter with reference to the drawings. First, a configuration of a reagent preparing device 6 according to a first embodiment of the present invention will be described with reference to FIGS. 1 to 8. In the first embodiment, a case of using the reagent preparing device 6 according to the first embodiment of the present invention as one part of a blood sample processing system 1 for performing a blood test will be described.

Figure 1:
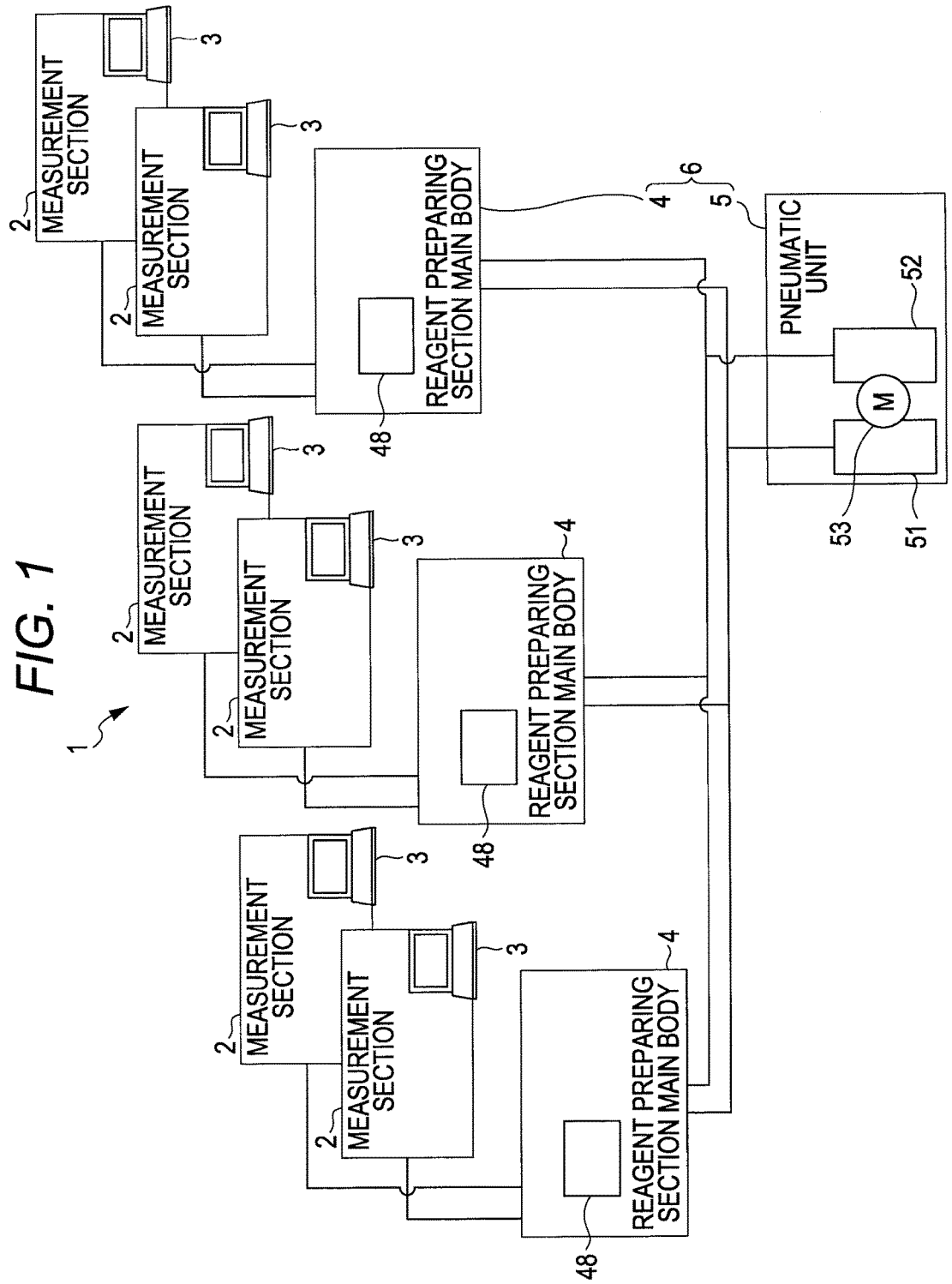
FIG. 1 is a schematic view showing a usage state of the reagent preparing device according to one embodiment of the present invention.

As shown in FIG. 1, the blood specimen processing system 1 is configured by six measurement sections 2 each having a function of measuring blood, six data processing sections 3 each for analyzing the measurement data output from each of the measurement sections 2 and obtaining an analysis result, and three reagent preparing devices 3 each for preparing a reagent to be used in the processing of specimens. Specifically, the reagent preparing device 6 is configured by a reagent preparing main body 4 and a pneumatic unit 5, where three reagent preparing main bodies 4 are connected to one pneumatic unit 5 by the flow path. Two measurement sections 2 are connected to each reagent preparing main body 4, and one data processing section 3 is connected to each measurement section 2.

Each measurement section 2 has a similar configuration, and is configured to measure white blood cells, reticulocytes, and blood platelets in the blood through the flow cytometry method. The measurement section 2 is configured to dilute the blood using a reagent prepared and supplied by the reagent preparing device 6 and to perform measurements on white blood cells, reticulocytes, and blood platelets. The measurement section 2 is also configured to clean a sampling valve 21b, a reaction chamber 21c and the like arranged in a sample preparing unit 21, as well as a sheath flow cell 22c and the like arranged in a detection unit 22, which are to be hereinafter described, using the reagent prepared and supplied by the reagent preparing device 6 as a cleaning fluid. The flow cytometry method is a measurement method of particles (blood cells) for detecting the forward scattered light, the lateral scattered light, and the lateral fluorescence emitted by the particles (blood cells) in the measurement sample by forming a sample flow including the measurement sample and irradiating the sample flow with laser light.

Figure 2:
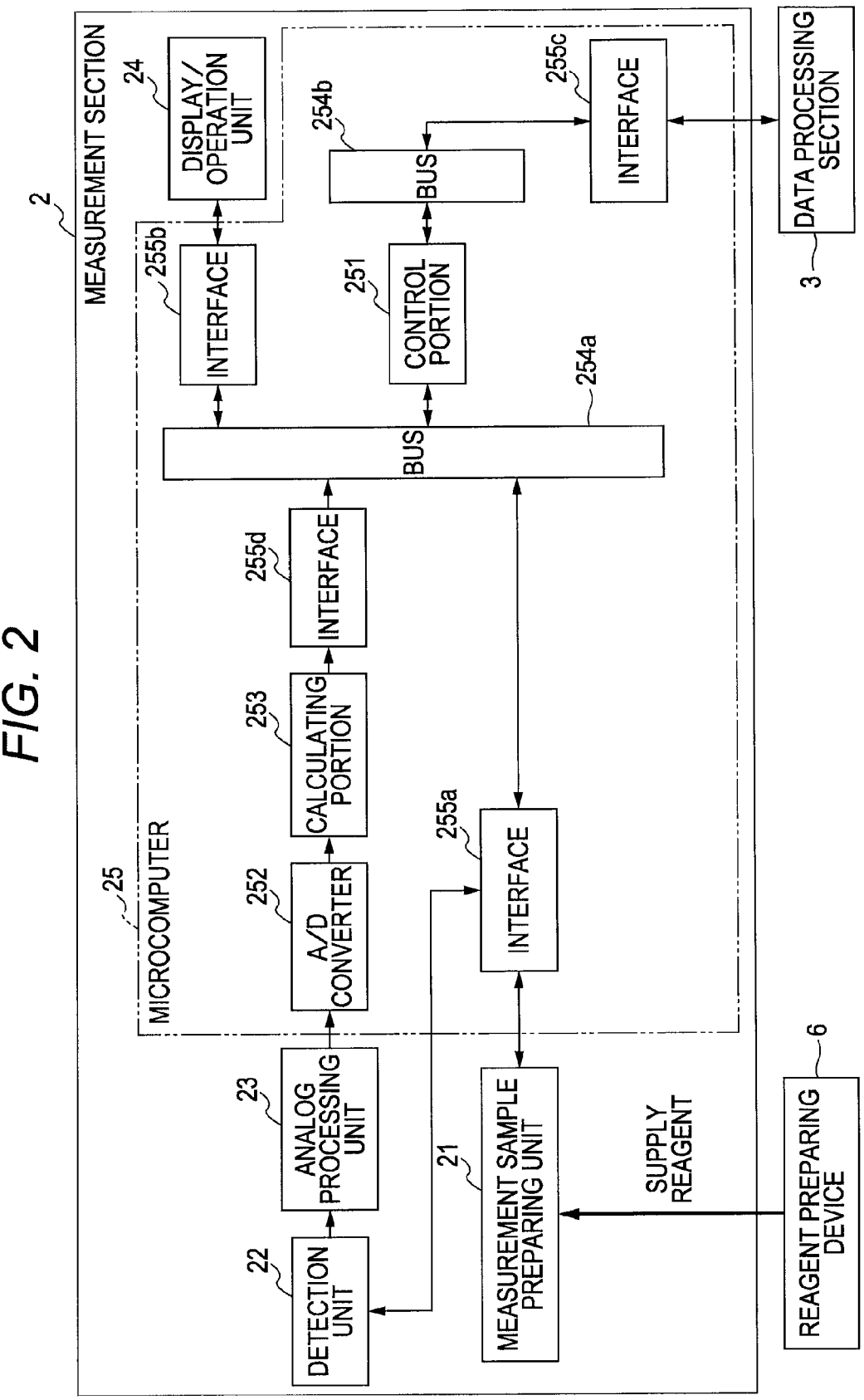
FIG. 2 is a block diagram showing a configuration of the blood specimen processing system including the reagent preparing device according to one embodiment of the present invention.

As shown in FIG. 2, the measurement section 2 includes a measurement sample preparing unit 21, a detection unit 22 for performing a measurement of the measurement sample, an analog processing unit 23 with respect to the output of the detection unit 22, a display/operation unit 24, and a microcomputer 25 for controlling the measurement section 2.

Figure 3:
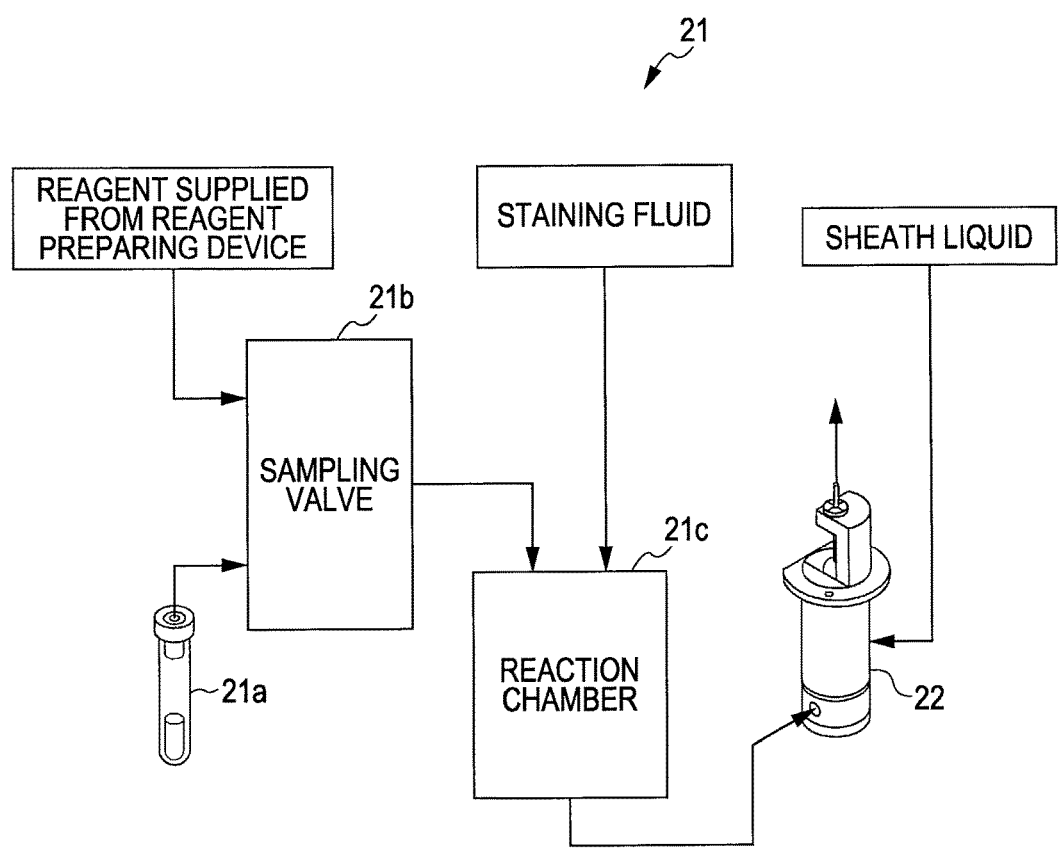
FIG. 3 is a view for describing a specimen preparing section of the blood specimen processing system including the reagent preparing device according to one embodiment of the present invention.

The measurement sample preparing unit 21 is arranged to prepare a white blood cell measurement sample, a reticulocyte measurement sample, and a blood platelet measurement sample. As shown in FIG. 3, the measurement sample preparing unit 21 includes the sampling valve 21b for aspirating blood and the reaction chamber 21c. A blood collecting tube 21a stores the blood to be analyzed.

The sampling valve 21b has a function of quantifying the blood of the blood collecting tube 21a aspirated by an aspiration pipette (not shown) by a predetermined amount. The sampling valve 21b is configured so that a predetermined reagent can be mixed with the aspirated blood. That is, the sampling valve 21b is configured so that a diluted sample in which a predetermined amount of reagent supplied from the reagent preparing device 6 is mixed in a predetermined amount of blood can be generated.

The reaction chamber 21c is configured so that a predetermined staining fluid is further mixed to the diluted sample supplied from the sampling valve 21b and reacts with it for a predetermined time. The measurement sample preparing unit 21 thus has a function of preparing the white blood cell measurement sample in which the white blood cells are stained and the red blood cells are hemolyzed. The measurement sample preparing unit 21 also has a function of preparing the reticulocyte measurement sample in which the reticulocyte is stained and a function of preparing the blood platelet measurement sample in which the blood platelet is stained.

The measurement sample preparing unit 21 is also configured to supply the white blood cell measurement sample with the sheath liquid from the measurement sample preparing unit 21 to the sheath flow cell 22c described later (see FIG. 4) at the time of a white blood cell differential measurement (hereinafter also referred to as "DIFF measurement") mode. The measurement sample preparing unit 21 is also configured to supply the reticulocyte measurement sample with the sheath liquid from the measurement sample preparing unit 21 to the sheath flow cell 22c at the time of a reticulocyte measurement (hereinafter also referred to as "RET measurement") mode. Furthermore, the measurement sample preparing unit 21 is also configured to supply the blood platelet measurement sample with the sheath liquid from the measurement sample preparing unit 21 to the sheath flow cell 22c at the time of a blood platelet measurement (hereinafter also referred to as "PLT measurement") mode.

Figure 4:
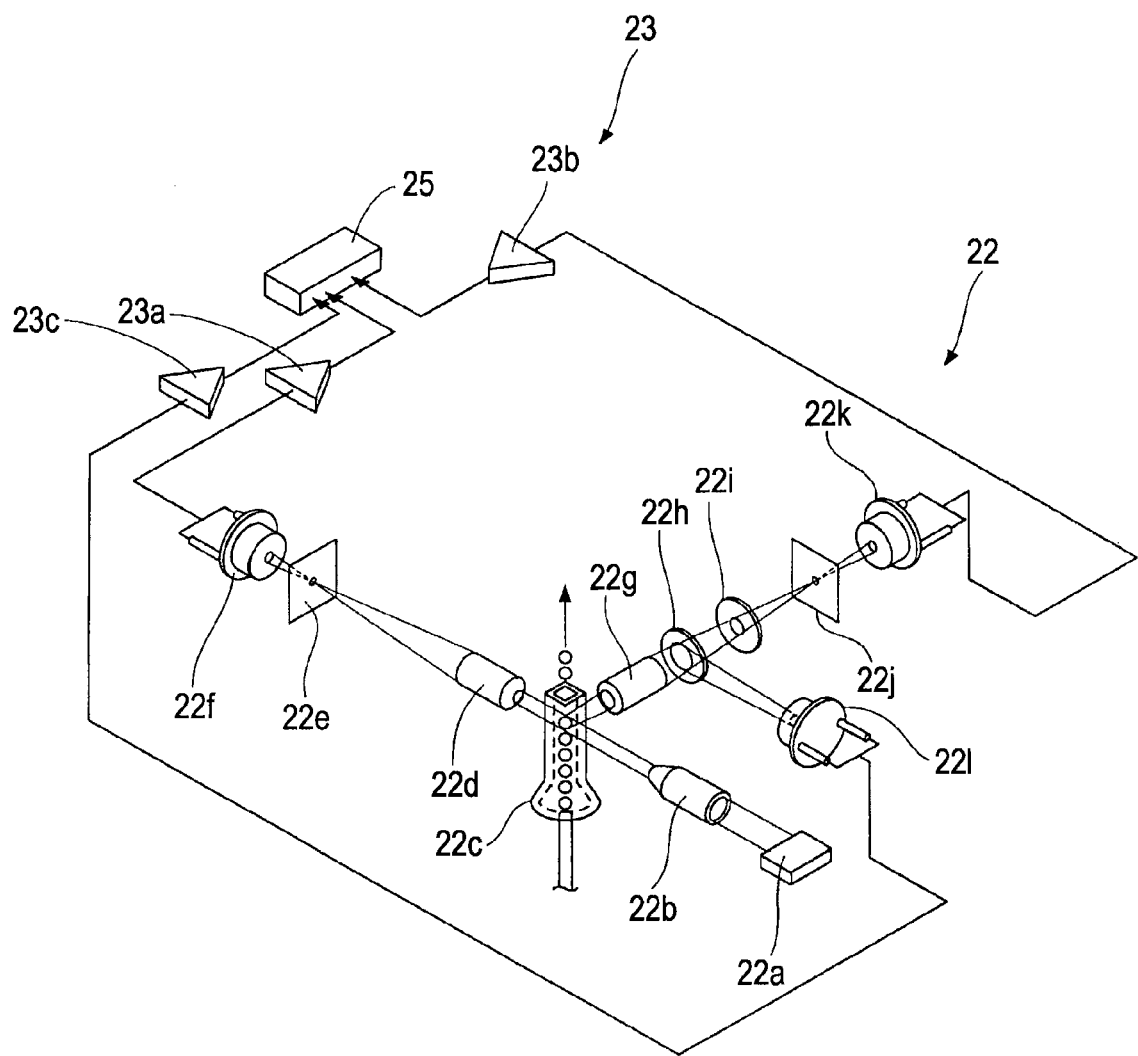
FIG. 4 is a schematic view showing a detection unit of the blood specimen processing system including the reagent preparing device according to one embodiment of the present invention.

As shown in FIG. 4, the detection unit 22 includes a light emitting portion 22a for emitting laser light, an irradiation lens unit 22b, the sheath flow cell 22c irradiated with laser light, a light collecting lens 22d arranged on an extended line in a direction the laser light emitted from the light emitting potion 22a advances, a pin hole 22e and a PD (Photo Diode) 22f, a light collecting lens 22g arranged in a direction intersecting the direction the laser light emitted from the light emitting portion 22a advances, a dichroic mirror 22h, an optical filter 22i, a pin hole 22j and an APD (Avalanche Photo Diode) 22k, and a PD 22l arranged at the side of the dichroic mirror 22h.

The light emitting portion 22a is arranged to emit light to the sample flow including the measurement sample that passes the inside of the sheath flow cell 22c. The irradiation lens unit 22b is arranged to convert the light emitted from the light emitting portion 22a to parallel light. The PD 22f is arranged to receive the forward scattered light output from the sheath flow cell 22c. The information on the size of the particle (blood cell) in the measurement sample can be obtained from the forward scattered light output from the sheath flow cell 22c.

The dichroic mirror 22h is arranged to separate the lateral scattered light and the lateral fluorescence output from the sheath flow cell 22c. Specifically, the dichroic mirror 22h is arranged to have the lateral scattered light output from the sheath flow cell 22c enter to the PD 22i, and to have the lateral fluorescence output from the sheath flow cell 22c enter to the APD 22k. The PD 22i is arranged to receive the lateral scattered light. Internal information, for example, the size of the core of the particle (blood cell) in the measurement sample can be obtained from the lateral scattered light output from the sheath flow cell 22c. The APD 22k is arranged to receive the lateral fluorescence. Information on the staining degree of the particle (blood cell) in the measurement sample can be obtained from the lateral fluorescence output from the sheath flow cell 22c. The PD 22f, 22l, and the APD 22k respectively have a function of converting the received optical signal to an electrical signal.

As shown in FIG. 4, the analog processing unit 23 includes amplifiers 23a, 23b, and 23c. The amplifiers 23a, 23b, and 23c are respectively arranged to perform amplification and waveform processing on the electrical signal output from the PD 22f, 22i, and the APD 22k.

As shown in FIG. 2, the microcomputer 25 includes a control portion 251 including a control processor and a memory for operating the control processor, an A/D converter 252 for converting a signal output from the analog processing unit 23 to a digital signal, and a calculating portion 253 for performing a predetermined process on the digital signal output from the A/D converter 252.

The control portion 251 has a function of controlling the measurement sample preparing unit 21 and the detection unit 22 through a bus 254a and an interface 255a. The control portion 251 is connected with the display/operation unit 24 through the bus 254a and an interface 255b, and connected with the data processing section 3 through a bus 254b and an interface 255c. The calculating portion 253 has a function of outputting a calculation result to the control portion 251 through an interface 255d and the bus 254a. The control portion 251 has a function of transmitting the calculation result (measurement data) to the data processing section 3.

Figure 5:
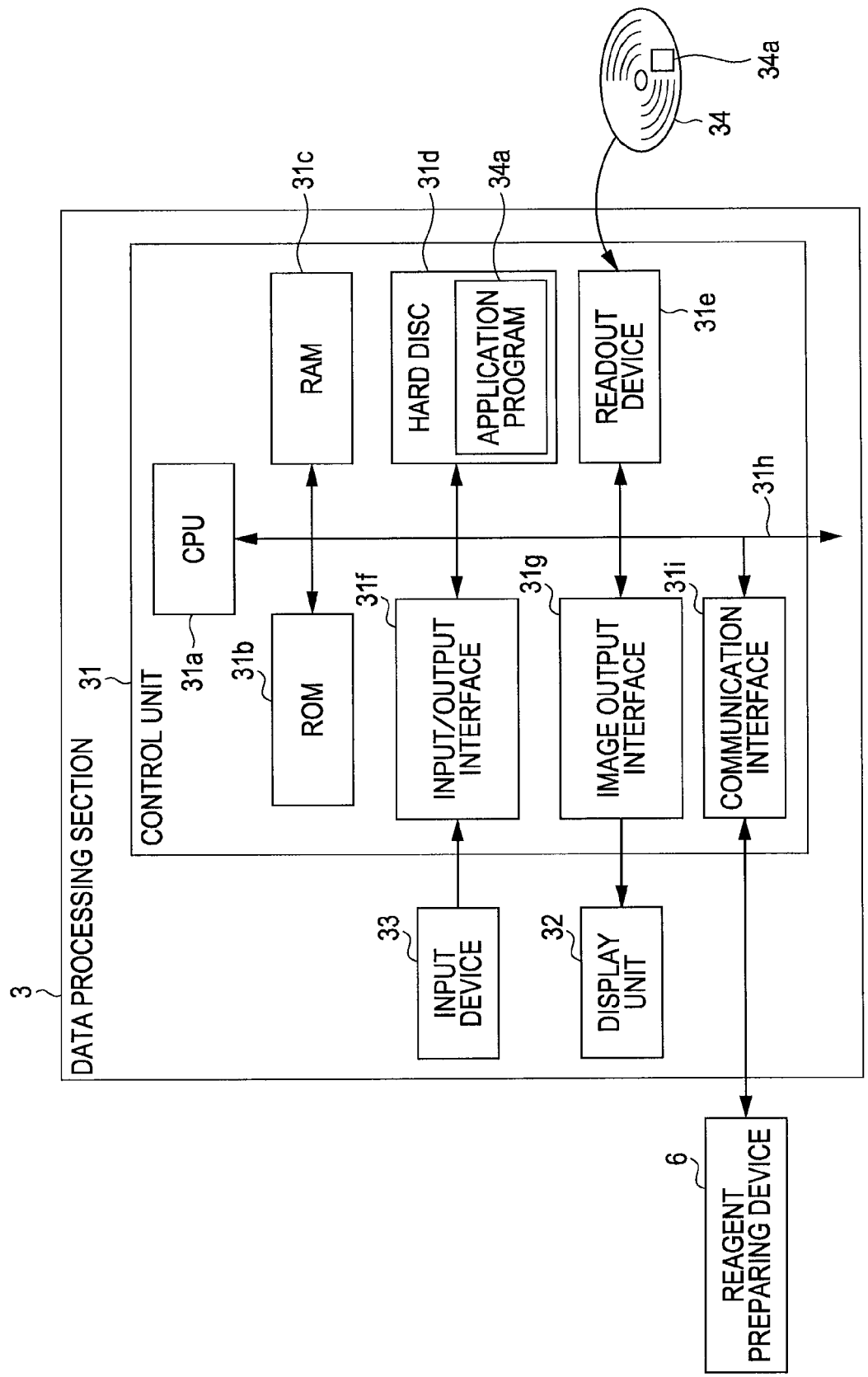
FIG. 5 is a block diagram showing a configuration of a data processing section of the blood specimen processing system including the reagent preparing device according to one embodiment of the present invention.

As shown in FIG. 1, the data processing section 3 includes a personal computer (PC) and the like, and has a function of analyzing the measurement data of the measurement section 2 and displaying the analysis result. Furthermore, six data processing sections 3 have similar configuration with respect to each other, and includes a control unit 31, a display unit 32, and an input device 33, as shown in FIG. 5.

The control unit 31 has a function of transmitting a measurement start signal including the measurement mode information and a shutdown signal to the measurement section 2. As shown in FIG. 5, the control unit 31 is also configured by a CPU 31a, a ROM 31b, a RAM 31c, a hard disc 31d, a readout device 31e, an input/output interface 31f, an image output interface 31g and a communication interface 31i. The CPU 31a, the ROM 31b, the RAM 31c, the hard disc 31d, the readout device 31e, the input/output interface 31f, the image output interface 31g and the communication interface 31i are connected by a bus 31h.

The CPU 31a is arranged to execute computer programs stored in the ROM 31b and the computer programs loaded in the RAM 31c. The ROM 31b is configured by mask ROM, PROM, EPROM, EEPROM, and the like, and is recorded with computer programs to be executed by the CPU 31a, data used for the same, and the like.

The RAM 31c is configured by SRAM, DRAM and the like. The RAM 31c is used to read out the computer programs recorded on the ROM 31b and the hard disc 31d. The RAM 31c is used as a work region of the CPU 31a when executing the computer programs.

The hard disc 31d is installed with various computer programs to be executed by the CPU 31a such as operating system and application program, as well as data used in executing the computer program. The application program 34a described later is also installed in the hard disc 31d.

The readout device 31e is configured by flexible disc drive, CD-ROM drive, DVD-ROM drive and the like, and is able to read out computer programs and data recorded on a portable recording medium 34. The application program 34a causing the computer to implement a predetermined function is stored in the portable recording medium 34. The computer serving as the data processing section 3 reads out the application program 34a from the portable recording medium 34, and installs the application program 34a to the hard disc 31d. The application program 34a includes an analysis program for analyzing the specimen measured by the measurement section, and outputting the analysis result as an analysis result of the specimen.

The application program 34a is not only provided by the portable recording medium 34, and may be provided through an electrical communication line (wired or wireless) from external devices communicably connected with the data processing section 3 by the electrical communication line. For instance, the application program 34a may be stored in the hard disc of the server computer on the Internet, wherein the data processing section 3 can access the server computer to download the application program 34a and install the application program 34a in the hard disc 31d.

Operating system providing graphical user interface environment such as Windows (registered trademark) manufactured and sold by US Microsoft Co. is installed in the hard disc 31d. In the following description, the application program 34a according to the first embodiment is assumed to be operating on the operating system.

The input/output interface 31f is configured by serial interface such as USB, IEEE1394 and RS-232C; parallel interface such as SCSI, IDE and IEEE1284; analog interface such as a D/A converter and an A/D converter, and the like. The input device 33 including a keyboard and a mouse is connected to the input/output interface 31f, so that the user can input data to the data processing section 3 using the input device 33. The user can also select the measurement mode, and activate and shut down the measurement section 2 using the input device 33.

The image output interface 31g is connected to the display unit 32 configured by LCD, CRT or the like, and is configured to output a video signal corresponding to the image data provided from the CPU 31a to the display unit 32. The display unit 32 displays the image (screen) according to the input video signal.

Figure 6:
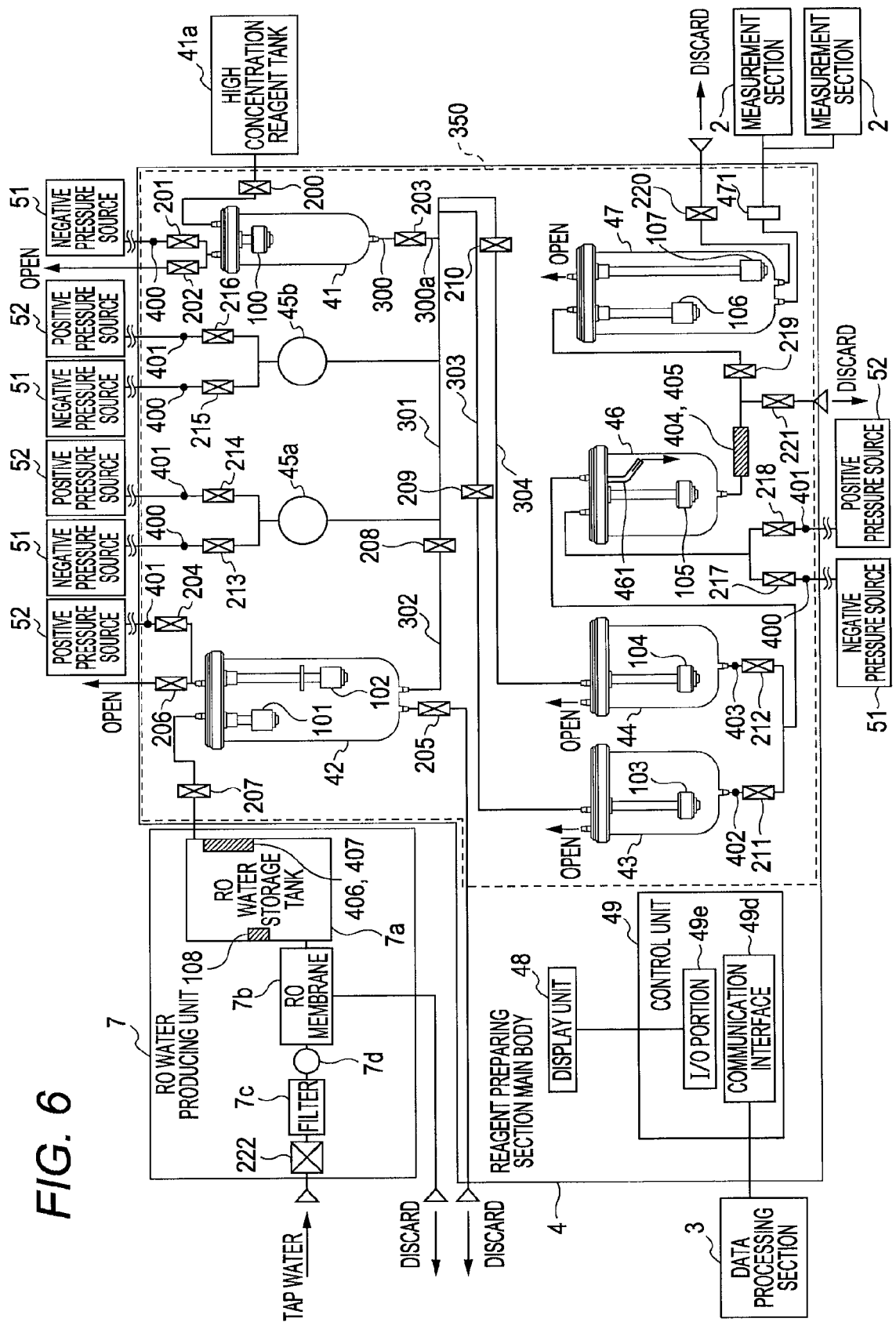
FIG. 6 is a block diagram showing a configuration of the reagent preparing device according to one embodiment of the present invention.

The reagent preparing device 6 is arranged to prepare the reagent to be used in the measurement specimen preparing section 21 of the measurement section 2. Specifically, as shown in FIG. 6, the reagent preparing device 6 is configured to prepare the reagent to be used in blood analysis by diluting the high concentration reagent to the desired concentration using the RO water produced by the RO water producing unit 7 arranged outside. The RO water is one type of pure water and is water in which impurities are removed by being transmitted through an RO (Reverse Osmosis)

membrane (reverse osmosis membrane). Other than the RO water, the pure water includes purified water, deionized water and distilled water, and is water subjected to the process of removing impurities, and the purity is not particularly limited. The high concentration reagent is a reagent undiluted solution, where the concentration of the contained component is higher than the reagent supplied to the measurement section 2.

Three reagent preparing main bodies 4 have a configuration similar to each other, and includes a high concentration reagent chamber 41, a RO water chamber 42, and two diluting chambers 43 and 44, two diaphragm pumps 45a and 45b, a stirring chamber 46, a supply chamber 47, ad display unit 48, a control unit 49 for controlling the operation of each unit of the reagent preparing device 6, electromagnetic valves 200 to 221, flow paths 300, 300a, 301 to 304, pressure sensors 400, 401, air bubble sensors 402, 403, a conductivity sensor 404, and a filter 471, as shown in FIG. 6. The reagent preparing section 350 for executing the reagent preparation operation of preparing the reagent is configured by the high concentration reagent chamber 41, the RO water chamber 42, two diluting chambers 43 and 44, the two diaphragm pumps 45a and 45b, the stirring chamber 46, the supply chamber 47, the electromagnetic valves 200 to 221, the flow paths 300, 300a, 301 to 304, the pressure sensors 400, 401, the air bubble sensors 402, 403, the conductivity sensor 404, and the filter 471. It should be recognized that the configuration of the reagent preparing section 350 is not limited to the present embodiment, and may be appropriately changed by the configuration of the reagent preparing main body 4. The three reagent preparing main bodies 4 are connected to a common pneumatic unit 5 (see FIG. 1) installed exterior to the housing, and is configured to transfer each liquid in the device using the negative pressure force and the positive pressure force supplied from the pneumatic unit 5. The three reagent preparing main bodies 4 are configured to execute the reagent preparation operation independent from each other.

The high concentration reagent chamber 41 is configured to supply the high concentration reagent from a high concentration reagent tank 41a. The high concentration reagent chamber 41 includes a float switch 100 for detecting that a predetermined amount of high concentration reagent is stored in the chamber. The float switch 100 is configured such that the float portion moves up and down according to the liquid amount (liquid level) in the high concentration reagent chamber 41. Each unit is controlled by the control unit 49 such that the high concentration reagent is supplied from the high concentration reagent tank 41a to the high concentration reagent chamber 41 when the float portion of the float switch 100 reaches the lower limit. Furthermore, each unit is controlled by the control unit 49 such that the supply of the high concentration reagent from the high concentration reagent tank 41a to the high concentration reagent chamber 41 is stopped when the float portion of the float switch 100 reaches the upper limit. The float switch 100 is arranged near the upper end of the high concentration reagent chamber 41, and is configured such that the float portion reaches the upper limit when about 300 mL of the high concentration reagent is stored in the high concentration reagent chamber 41. The high concentration reagent is thus supplied such that about 300 mL is stored in the high concentration reagent chamber 41 on a constant basis.

The high concentration reagent chamber 41 is connected to the high concentration reagent tank 41a through an electromagnetic valve 200, and is connected to the negative pressure source 51 of the pneumatic unit 5 through an electromagnetic valve 201. A pressure sensor 400 for detecting the magnitude of the negative pressure force supplied from the negative pressure source 51 is arranged between the negative pressure source 51 and the electromagnetic valve 201. The high concentration reagent chamber 41 is also configured to be opened to atmosphere or closed by the opening and closing of the electromagnetic valve 202. The high concentration reagent chamber 41 is connected to a flow path 301 for transferring the liquid from the diaphragm pump 45a (45b) to the diluting chamber 43 (44) by the flow path 300. An electromagnetic valve 203 is arranged on the flow path 300, which electromagnetic valve 203 is arranged near the flow path 301. Specifically, the length of the flow path 300a between the electromagnetic valve 203 and the flow path 301 is set to a small length of about 15 mm. The flow path 300 (300a) connected to the high concentration reagent chamber 41 has an inner diameter of about 1.8 mm, and the flow path 301 has an inner diameter of about 4.0 mm.

The RO water chamber 42 is configured such that the RO water for diluting the high concentration reagent is supplied from the RO water producing unit 7. The RO water chamber 42 includes float switches 101 and 102 for detecting that the RO water stored in the chamber has reached the upper limit amount and the lower limit amount, respectively. The float switch 101 (102) is configured such that the float portion moves up and down according to the liquid amount (liquid level) in the RO water reagent chamber 42. Each unit is controlled by the control unit 49 such that the supply of RO water from the RO water producing unit 7 to the RO water chamber 42 is stopped when the float portion of the float switch 101 reaches the position corresponding to the upper limit amount of the RO water chamber 42. Furthermore, each unit is controlled by the control unit 49 such that the RO water is supplied from the RO water producing unit 7 to the RO water chamber 42 when the float portion of the float switch 102 reaches the position corresponding to the lower limit amount of the RO water chamber 42.

The float switch 101 is arranged near the upper end of the RO water chamber 42, and is configured such that the float portion reaches the position corresponding to the upper limit amount of the RO water chamber 42 when about 600 mL of the RO water is stored in the RO water chamber 42. The float switch 102 is configured such that the float portion reaches the position corresponding to the lower limit amount of the RO water chamber 42 when the RO water stored in the RO water chamber 42 reduces to about 300 mL. The RO water chamber 42 stores the RO water of greater than or equal to about 300 mL and smaller than or equal to about 600 mL on a constant basis.

The RO water chamber 42 is configured so that the RO water in the chamber can be discarded. Specifically, the RO water chamber 42 is connected to the positive pressure source 52 of the pneumatic unit 5 through the electromagnetic valve 204 and connected to a discard flow path through the electromagnetic valve 205, so that the RO water inside is pushed out to the discard flow path by the positive pressure force by opening both electromagnetic valves 204 and 205. A pressure sensor 401 for detecting the magnitude of the positive pressure force supplied from the positive pressure source 52 is arranged between the positive pressure source 52 and the electromagnetic valve 204. The RO water chamber 42 is configured to be opened to atmosphere and closed by the opening and closing of the electromagnetic valve 206. The RO water chamber 42 is connected to the RO water storage tank 7a, to be hereinafter described, of the RO water producing unit 7 through the electromagnetic valve 207. The RO water chamber 42 is connected to the diaphragm pumps 45a and 45b by the flow path 302 through the electromagnetic valve 208.

The diluting chambers 43 and 44 are respectively arranged to dilute the high concentration reagent with the RO water. As hereinafter described, the diluting chamber 43 (44) is configured to store about 300 mL of liquid (mixed solution of high concentration reagent and RO water) sent by the diaphragm pumps 45a and 45b. The diluting chamber 43 (44) includes a float switch 103 (104) for detecting that the remaining amount of the liquid (mixed solution of high concentration reagent and RO water) stored in the chamber has reached a predetermined amount. The float switch 103 (104) is configured such that the float portion moves up and down according to the liquid amount (liquid level) in the diluting chamber 43 (44). The diluting chamber 43 (44) is configured so as to be always opened to atmosphere. The diluting chamber 43 (44) is connected to the flow path 301 by the flow path 303 (304) through the electromagnetic valve 209 (210). The flow path 303 (304) has an inner diameter of about 4 mm, similar to the flow path 301. The liquid (RO water and high concentration reagent) transferred through the flow path 301 can be transferred to the diluting chamber 43 by opening the electromagnetic valve 209 with the electromagnetic valve 210 closed. The liquid (RO water and high concentration reagent) transferred through the flow path 301 can be transferred to the diluting chamber 44 by opening the electromagnetic valve 210 with the electromagnetic valve 209 closed. In other words, the electromagnetic valves 209 and 210 are respectively configured to function as a flow path switching unit of the flow paths 303 and 304.

The diluting chamber 43 (44) is connected to the stirring chamber 46 through the electromagnetic valve 211 (212). An air bubble sensor 402 (403) is arranged between the diluting chamber 43 (44) and the electromagnetic valve 211 (212). The air bubble sensor 402 (403) is a transmissive sensor, and is configured to detect air bubbles that pass the flow path. That the liquid (mixed solution of high concentration reagent and RO water) in the diluting chamber 43 (44) are all discharged can be checked by the control unit 49 when the float portion of the float switch 103 (104) reaches the lower limit and the air bubbles are detected by the air bubble sensor 402 (403). When the diluting chamber 43 (44) becomes empty (all liquid in the chamber is discharged), each unit is controlled by the control unit 49 so that the high concentration reagent and the RO water are supplied to the empty diluting chamber 43 (44).

The diaphragm pumps 45a and 45b have similar configuration with respect to each other, and are configured to perform the same operation at the same time. The diaphragm pump 45a (45b) has a function of quantifying about 6 mL (total of about 12 mL with two pumps) (constant amount) of liquid (high concentration reagent or RO water) in one quantifying operation. The diaphragm pump 45a (45b) is connected to the negative pressure source 51 through the electromagnetic valve 213 (215), and also connected to the positive pressure source 52 through the electromagnetic valve 214 (216). The pressure sensor 400 for detecting the magnitude of the negative pressure force supplied from the negative pressure source 51 is arranged between the negative pressure source 51 and the electromagnetic valve 213 (215), and the pressure sensor 401 for detecting the magnitude of the positive pressure force supplied from the positive pressure source 52 is arranged between the negative pressure source 52 and the electromagnetic valve 214 (216).

As shown in FIG. 6, the stirring chamber 46 is configured to accommodate about 300 mL of liquid, and is arranged to stir the liquid (mixed solution of high concentration reagent and RO water) transferred from the diluting chamber 43 (44). Specifically, the stirring chamber 46 includes a bent pipe 461, and is configured so that the liquid (mixed solution of high concentration reagent and RO water) transferred from the diluting chamber 43 (44) flows into the stirring chamber 46 along the inner wall surface of the stirring chamber 46 by passing the pipe 461. The liquid (mixed solution of high concentration reagent and RO water) transferred from the diluting chamber 43 (44) thus flows along the inner wall surface of the stirring chamber 46, whereby convection occurs and the high concentration reagent and the RO water are easily stirred. The high concentration reagent and the RO water are stirred to a certain extent in the diluting chamber 43 (44) and in the flow path from the diluting chamber 43 (44) to the stirring chamber 46, but the solution is more reliably stirred by configuring the stirring chamber 46 in the above manner.

The stirring chamber 46 includes a float switch 105 for detecting that the remaining amount of the liquid (mixed solution of high concentration reagent and RO water) accommodated in the chamber has reached a predetermined amount. The float switch 105 is configured such that the float portion moves up and down according to the liquid amount (liquid level) in the stirring chamber 46. Each unit is controlled by the control unit 49 such that about 300 mL of mixed solution is supplied from either diluting chamber 43 or 44 to the stirring chamber 46 when the float portion of the float switch 105 reaches the lower limit and the interior of the chamber becomes empty. When the mixed solution supplied from either diluting chamber 43 or 44 and stirred is discharged from the stirring chamber 46, about 300 mL of mixed solution is then supplied from the other diluting chamber 43 or 44 to the stirring chamber 46. The stirring chamber 46 is connected to the negative pressure source 51 through the electromagnetic valve 217, and connected to the positive pressure source 52 through the electromagnetic valve 218. The pressure sensor 400 for detecting the magnitude of the negative pressure force supplied from the negative pressure source 51 is arranged between the negative pressure source 51 and the electromagnetic valve 217, and the pressure sensor 401 for detecting the magnitude of the positive pressure force supplied from the positive pressure source 52 is arranged between the positive pressure source 52 and the electromagnetic valve 218.

The supply chamber 47 is arranged to store a predetermined amount of reagent to supply to the measurement section 2. The supply chamber 47 has an accommodation capacity of about 600 mL. The supply chamber 47 includes a float switch 106 for detecting that the remaining amount of reagent stored in the chamber has reached about 300 mL The supply chamber 47 also includes a float switch 107 for detecting that the remaining amount of reagent stored in the supply chamber 47 is substantially zero. The float switch 106 (107) is configured such that the float portion moves up and down according to the liquid amount (liquid level) in the supply chamber 47. The float portion of the float switch 106 is configured to be movable from the vicinity of the upper end in the height direction of the supply chamber 47 to the intermediate position. Each unit is controlled by the control unit 49 so that about 300 mL of reagent of the desired concentration is supplied from the stirring chamber 46 to the supply chamber 47 when the float portion of the float switch 106 reaches the intermediate position in the height direction of the supply chamber 47 (lower limit position in the movable range of the float portion of the float switch 106). The reagent of desired concentration of greater than or equal to about 300 mL and less than or equal to about 600 mL is stored in the supply chamber 47 on a constant basis. Thus, the reagent can be rapidly supplied to the measurement section 2 by storing a predetermined amount of reagent in the supply chamber 47.

The float portion of the float switch 107 is configured to be movable to the vicinity of the bottom of the supply chamber 47. The supply of reagent to the measurement section 2 is stopped when detected that the remaining amount of reagent accommodated in the chamber is substantially zero by the float switch 107. Therefore, the air bubbles are prevented from mixing to the reagent to be supplied to the measurement section 2 while continuing the supply of reagent to the measurement section 2 as much as possible even if the reagent is not transferred to the supply chamber 47 for some reasons.

The supply chamber 47 is connected to the stirring chamber 46 through the electromagnetic valve 219. The supply chamber 47 is configured so that the reagent in the chamber can be discarded at the time of maintenance and the like by opening the electromagnetic valve 220. The supply chamber 47 is configured so as to be opened to atmosphere on a constant basis. The supply chamber 47 is connected to the measurement section 2 through the filter 471. The filter 471 is arranged to prevent impurities from mixing in the reagent to be supplied to the measurement section 2.

A conductivity sensor 404 for measuring the electrical conductivity of the reagent is arranged between the stirring chamber 46 and the supply chamber 47. The conductivity sensor 404 includes a temperature sensor 405 for measuring the temperature of the reagent at the position where the conductivity sensor 404 is arranged. A discard flow path is connected between the conductivity sensor 404 and the electromagnetic valve 219 through the electromagnetic valve 221.

As shown in FIG. 1, the display unit 48 is arranged on the outer surface of the reagent preparing main body 4. The display unit 48 is configured by a touch panel type liquid crystal display.

Figure 7:
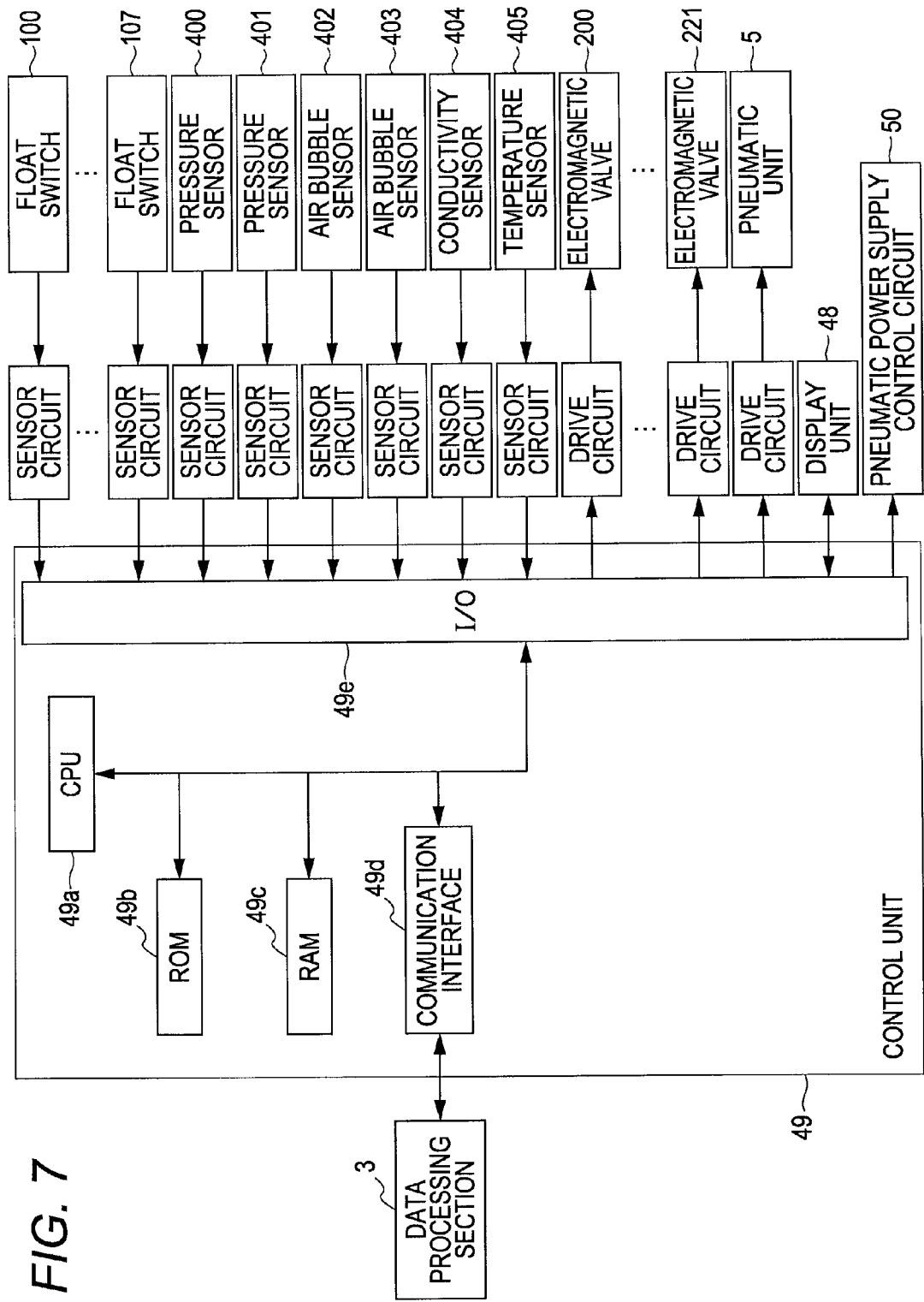
FIG. 7 is a block diagram explaining a control unit of the reagent preparing device according to one embodiment of the present invention.

As shown in FIG. 7, the control unit 49 includes a CPU 49a, a ROM 49b, a RAM 49c, a communication interface 49d connected to the data processing section 3, and an I/O (Input/Output) portion 49e connected to each unit in the reagent preparing device 4 through each circuit.

The CPU 49a can execute computer programs stored in the ROM 49b and the computer programs loaded in the RAM 49c. The CPU 49a is configured to use the RAM 49c as a work region when executing the computer programs.

A general formula for obtaining a target value of the electrical conductivity of the reagent is expressed with the following equation (1).

$$Z_0 = \{X + (A-1)Y\}/A \quad (1)$$

In the equation (1), $Z_0$ is, at 25° C., the target value (ms/cm) of the electrical conductivity of the reagent in which the high concentration reagent and the RO water are mixed and stirred, X is the electrical conductivity (ms/cm) of the high concentration reagent at 25° C., Y is the electrical conductivity (ms/cm) of the RO water at 25° C., and A is the diluting magnification (known) (25 times in the first embodiment). Here, X is a value unique to the high concentration reagent, and is a known value obtained through experiments and the like in advance.

The correction formula for taking into consideration the temperature of the RO water obtained by the temperature sensor 407 and the temperature of the reagent obtained by the temperature sensor 405 is expressed with the following equation (2).

$$Z = [\{X + (A-1)Y\}/A] \times \{1 + \alpha 1(T2-25)\} = [[X + (A-1)Y1/\{1 + \alpha 0(T1-25)\}]/A] \times \{1 + \alpha 1(T2-25)\} \quad (2)$$

In the equation (2), Z is, at T2° C., the target value (ms/cm) of the electrical conductivity of the reagent in which the high concentration reagent and the RO water are mixed and stirred, Y1 is the electrical conductivity of the RO water at T1° C., T1 is the temperature of the RO water (° C.), T2 is the temperature (° C.) of the reagent in which the high concentration reagent and the RO water are mixed and stirred, $\alpha 0$ is the temperature coefficient compared with the electrical conductivity of the RO water at 25° C., and $\alpha 1$ is the temperature coefficient compared with the electrical conductivity of the reagent in which the high concentration reagent and the RO water are mixed and stirred, at 25° C. The temperature coefficients $\alpha 0$ and $\alpha 1$ differ depending on the type and concentration of the liquid, but are 0.02 for simplification in JIS (Japanese Industrial Standards).

The CPU 49a is configured to calculate the target value Z from the equation (2). Therefore, the CPU 49a determines the target value based on the desired diluting magnification A (known), the detection value Y1 of the electrical conductivity of the RO water, the measurement value T1 of the temperature of the RO water, the measurement value T2 of the temperature of the mixed and stirred reagent, and the electrical conductivity X (known) of the high concentration reagent.

The CPU 49a is configured to accept the activation instruction and the shutdown instruction of the reagent preparing device 6 from the user through the touch panel type display unit 48.

The CPU 49a is configured to perform a control of ON/OFF switching the power supply for driving the motor 53 of the pneumatic unit 5. Specifically, the CPU 49a controls the ON and the OFF of the power supply for driving the motor 53 of the pneumatic unit 5 by supplying or not supplying the base current to the NPN bipolar transistor 50a of the pneumatic power supply control circuit 50, to be described later. The CPU 49a is configured to turn OFF the power supply for driving the motor 53 of the pneumatic unit 5 when the reagent preparing main body 4 is in standby state, that is, when the reagent preparation operation is not executed, and to turn ON the power supply for driving the motor 53 of the pneumatic unit 5 when the reagent preparation operation is executed. Each CPU 49a arranged in the three reagent preparing main bodies 4 is configured to turn ON the power supply for driving the motor 53 of the pneumatic unit 5 independent from each other. In other words, the power supply of the motor 53 of the pneumatic unit 5 is turned OFF only when all of the three CPUs 49a turn OFF the power supply of the motor 53 of the pneumatic unit 5.

The communication interface 49d is configured to transmit error information related to error that occurs in the reagent preparing device 6 to the data processing section 3. The error information includes information for urging replacement of the high concentration reagent tank 41a, information notifying that the RO water is no longer supplied, and information notifying the abnormality of the negative pressure source 51 and the positive pressure source 52.

As shown in FIG. 7, the I/O portion 49e is configured so that signals are input from the float switches 100 to 107, the air bubble sensors 402, 403, the conductivity sensor 404, and the temperature sensor 405 and the pressure sensors 400, 401 through each sensor circuit. The I/O portion 49e is configured to output signals to each drive circuit to control the drive of the electromagnetic valves 200 to 221 and the pneumatic unit 5 through each drive circuit. The I/O portion 49e is configured to receive the signal corresponding to the instruction of the user from the touch panel type display unit 48, and to output a video signal such as image data to the display unit 48.

Figure 8:
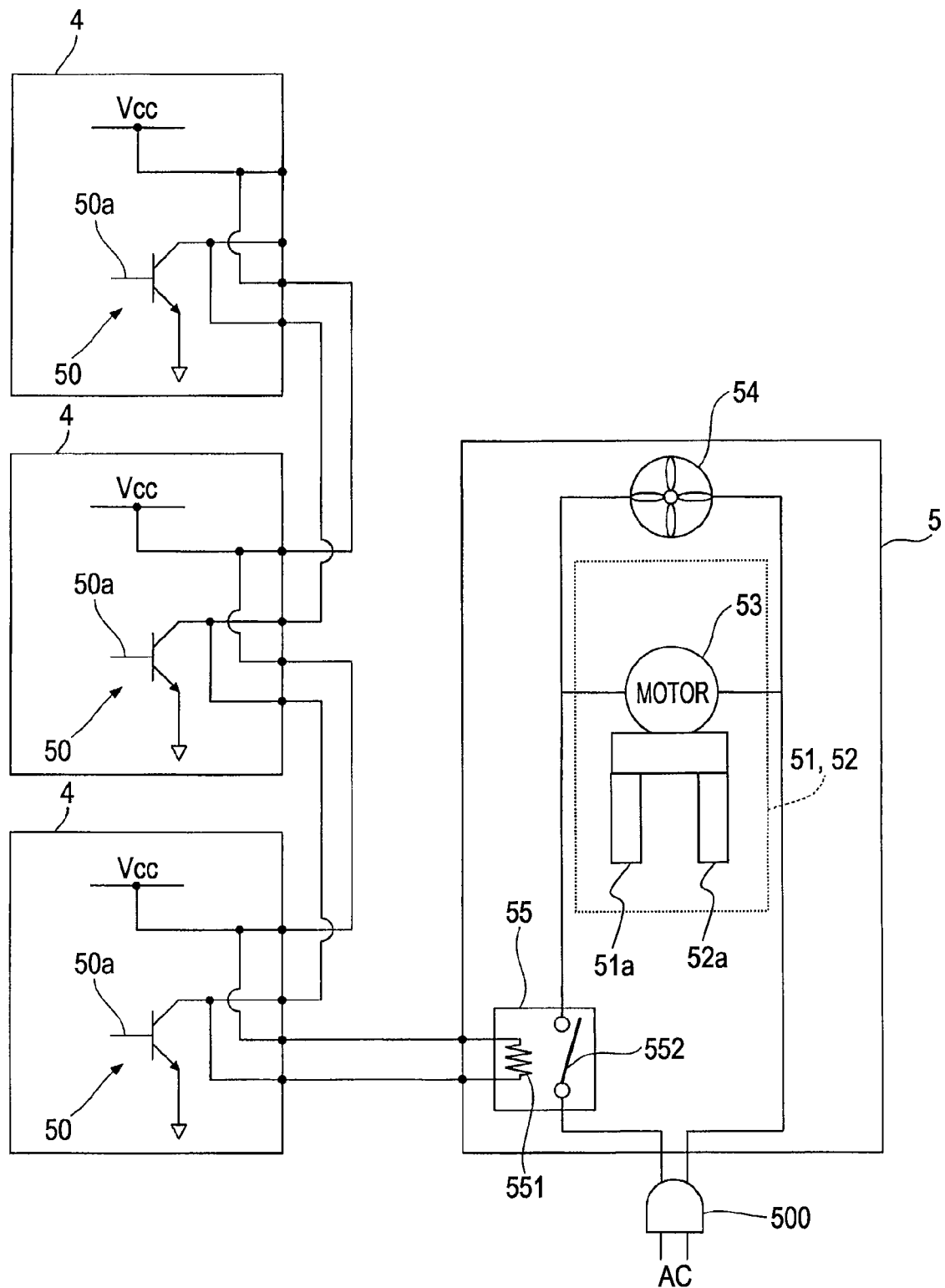
FIG. 8 is a schematic view showing an electrical connecting configuration of the reagent preparing device according to one embodiment of the present invention.

As shown in FIG. 8, each reagent preparing main body 4 is electrically connected to the pneumatic unit 5 directly or indirectly. Specifically, one of the three reagent preparing main bodies 4 is directly connected to the coil 551 of an electromagnetic relay 55, to be described later, of the pneumatic unit 5, and the other two reagent preparing main bodies 4 are indirectly connected to the coil 551 of the electromagnetic relay 55, to be described later, through the adjacent reagent preparing main body 4. Specifically, each reagent preparing main body 4 interiorly includes a pneumatic power supply control circuit 50 including the NPN bipolar transistor 50a, as shown in FIG. 8. The pneumatic power supply control circuit 50 of each reagent preparing main body 4 has the collector of the NPN bipolar transistor 50a directly or indirectly connected to one end of the coil 551 of the electromagnetic relay 55, to be described later, and the emitter of the NPN bipolar transistor 50a grounded. In the pneumatic power supply control circuit 50 of each reagent preparing main body 4, the power supply voltage Vcc is directly or indirectly connected to the other end of the coil 551 of the electromagnetic relay 55, to be described later. The NPN bipolar transistor 50a is turned ON by supplying the base current to the NPN bipolar transistor 50a, so that the current flows to the path to the collector and the emitter of the NPN bipolar transistor 50a from the power supply voltage Vcc through the coil 551 of the electromagnetic relay 55. The three reagent preparing main bodies 4 can flow current to the coil 551 of the electromagnetic relay 55 independent from each other by supplying the base current to each NPN bipolar transistor 50a. In other words, the current does not flow to the coil 551 of the electromagnetic relay 55 if the base current is not supplied to the NPN bipolar transistors 50a in all three reagent preparing main bodies 4.

As shown in FIG. 8, the pneumatic unit 5 of the reagent preparing device 6 includes the negative pressure source 51 and the positive pressure source 52 including a piston pump, the motor 53 for operating the negative pressure source 51 and the positive pressure source 52, the cooling fan 54 for cooling the temperature in the pneumatic unit 5, and the electromagnetic relay 55 for switching ON and OFF of the power supply of the motor 53 and the cooling fan 54.

The negative pressure source 51 and the positive pressure source 52 are configured to continuously generate the negative pressure force and the positive pressure force by reciprocate driving the piston (not shown) with the rotational drive of the motor 53. As shown in FIG. 1, the negative pressure source 51 and the positive pressure source 52 are connected to three reagent preparing main bodies 4 by way of the flow path, so that the generated negative pressure force and the positive pressure force are supplied to each reagent preparing main body 4.

The motor 53 is configured to operate the pistons 51a, 52a of both the negative pressure source 51 and the positive pressure source 52. The motor 53 is connected to the AC power supply 500 through the switch 552 of the electromagnetic relay 55. The motor 53 is supplied with current and driven when the electromagnetic relay 55 is in the conductive state (ON state), and is not supplied with current and is not driven when the electromagnetic relay 55 is in the non-conductive state (OFF state). In other words, the motor 53 is configured to be switched to drive or stop by the switch 552 of the electromagnetic relay 55.

Similar to the motor 53, the cooling fan 54 is connected to the AC power supply 500 through the switch 552 of the electromagnetic relay 55. In other words, the cooling fan 54 operates when the motor 53 is operating, and stops when the motor 53 is stopped. Thus, the cooling fan 54 is operated only when the motor 53 is operated and the temperature in the pneumatic unit 5 rises, and hence the power consumption can be reduced compared to when the cooling fan 54 is operated on a constant basis.

The electromagnetic relay 55 includes the coil 551, and the switch 552 arranged in the vicinity of the coil 551. The electromagnetic relay 55 is configured to be switchable to the conductive state (ON state) and the non-conductive state (OFF state). Specifically, the electromagnetic relay 55 is such that when current flows to the coil 551, the switch 552 moves by the electromagnetic force generated at the periphery of the coil 551 so as to be in the conductive state (ON state), and when the current supply to the coil 551 is stopped, the switch 552 is returned so as to be in the non-conductive state (OFF state).

With the reagent preparing main body 4 and the pneumatic unit 5 configured in the above manner, the CPU 49a arranged in each reagent preparing main body 4 switches the electromagnetic relay 55 of the pneumatic unit 5 to the conductive state (ON state) or the non-conductive state (OFF state) and controls the operation of the motor 53 by simply controlling whether or not to supply the base current to the NPN bipolar transistor 50a. In other words, the generating operation of the negative pressure force and the positive pressure force by the pneumatic unit 5 is executed or the generating operation is stopped when the CPU 49a supplies or stops the base current to the NPN bipolar transistor 50a.

The RO water producing unit 7 is configured so that the RO water serving as the diluting liquid for diluting the high concentration reagent can be produced using tap water. Furthermore, as shown in FIG. 6, the RO water producing unit 7 includes the RO water storage tank 7a, the RO water film 7b, and the filter 7c for protecting the RO film 7b by removing impurities contained in the tap water. Furthermore, the RO water producing unit 7 includes a high pressure pump 7d for applying high pressure to the water passed through the filter 7c so that water molecules transmit through the RO membrane 7b, and an electromagnetic valve 222 for controlling the supply of tap water.

The RO water storage tank 7a is arranged to store the RO water transmitted through the RO film 7b. The RO water storage tank 7a includes a float switch 108 for detecting that a predetermined amount of RO water is stored. The RO water storage tank 7a includes a conductivity sensor 406 for measuring the electrical conductivity of the RO water in the RO water storage tank 7a. The conductivity sensor 406 includes a temperature sensor 407 for measuring the temperature of the RO water.

The RO water producing unit 7 enables the tap water to reach the filter 7c by opening the electromagnetic valve 222. The RO water producing unit 7 can transmit the water passed through the filter 7c through the RO film 7b at high pressure by driving the high pressure pump 7d. The RO water producing unit 7 is configured to accommodate a predetermined amount of RO water in the RO water storage tank 7a based on the detection result of the float switch 108. The speed the RO water is supplied from the RO water producing unit 7 to the RO water storage tank 7a, that is, the production speed of the RO water by the RO water producing unit 7 is greater than or equal to about 20 L/hour and smaller than or equal to about 50 L/hour.

The reagent preparation processing operation of the reagent preparing device 4 according to the first embodiment of the present invention will now be described with reference to FIGS. 6, 9, and 10.

Figure 9:
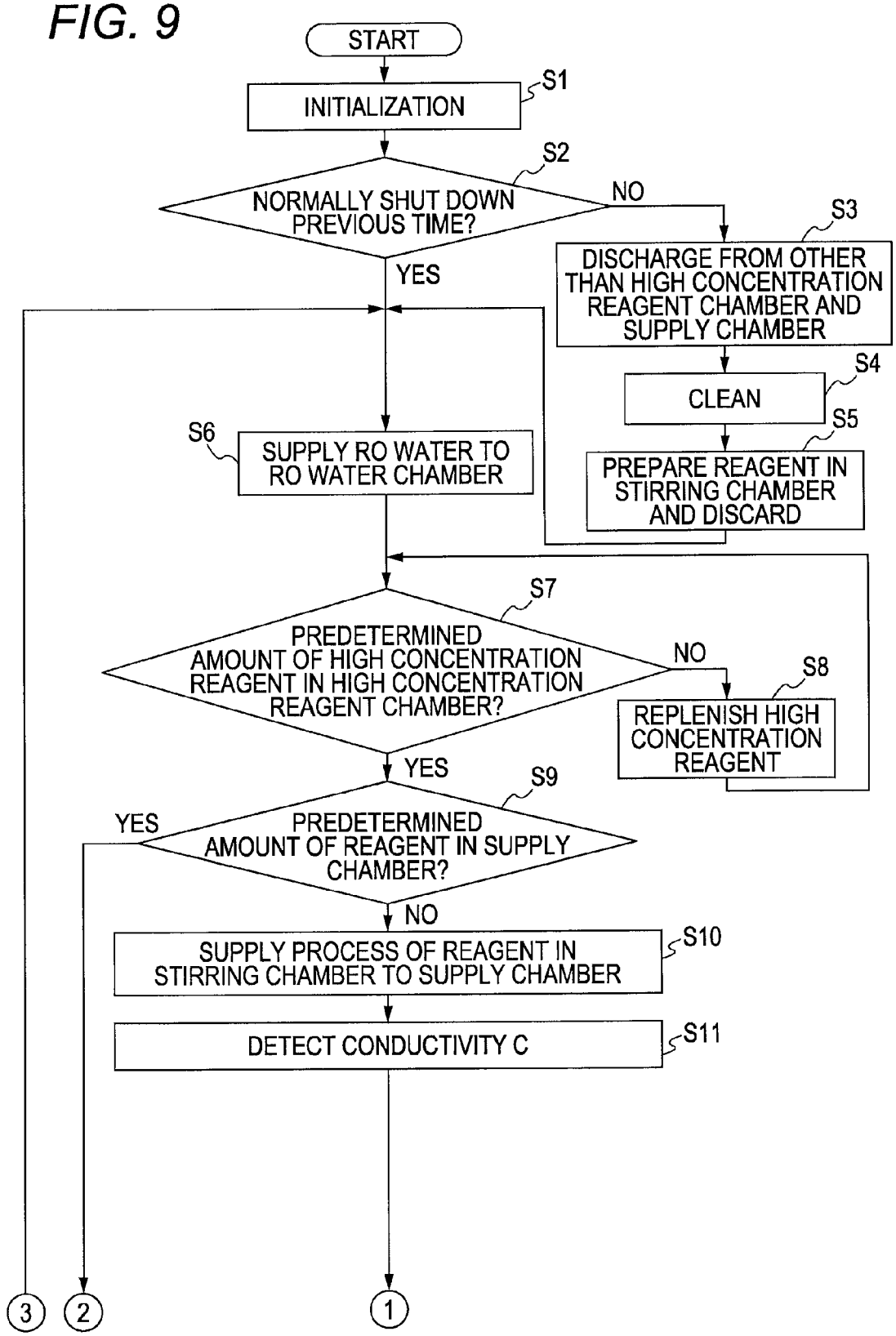
FIG. 9 is a flowchart explaining the reagent preparation processing operation of the reagent preparing device according to one embodiment of the present invention.

Initialization of the computer program stored in the ROM 49b is performed by the CPU 49a in step S1 of FIG. 9. In step S2, the CPU 49a determines whether or not the reagent preparing device 6 is normally shut down at the end of the previous operation. Specifically, determination is made based on a flag set to ON when normally shut down, as hereinafter described. The process proceeds to step S6 if normally shut down, and the process proceeds to step S3 if not normally shut down.

In step S3, the liquid in the chambers 42, 43, 44 and 46 other than the high concentration reagent chamber 41 and the supply chamber 47 are all discarded. Specifically, the electromagnetic valves 204 and 205 are opened with the electromagnetic valves 206, 207, and 208 closed by the CPU 49a to discard the RO water in the RO water chamber 42. The RO water discarded from the RO water chamber 42 may again be transferred to the RO water producing unit 7, and new RO water may be produced from the discarded RO water. Furthermore, the electromagnetic valves 218 and 221 are opened with the electromagnetic valves 211, 212, 217, and 219 closed by the CPU 49a to push out the mixed solution in the stirring chamber 46 to the discard flow path by the positive pressure force. The electromagnetic vales 211 and 217 are then opened with the electromagnetic valves 212, 218, 219, and 221 closed by the CPU 49a to transfer the mixed solution in the diluting chamber 43 to the stirring chamber 46 with the negative pressure force, and thereafter, the mixed solution is discarded from the stirring chamber 46 by the above-described operation. The mixed solution in the diluting chamber 44 also can be transferred to the stirring chamber 46 with the negative pressure force by opening the electromagnetic valves 212 and 217 with the electromagnetic valves 211, 218, 219, and 221 closed by the CPU 49a.

Therefore, the RO water having a possibility of being accumulated for a long time is prevented from being used in the reagent preparation, and the reagent of unknown diluting magnification is prevented from being prepared by discarding all liquids in the chambers 42, 43, 44, and 46 other than the high concentration reagent chamber 41 and the supply chamber 47 in step S3.

Thereafter, in step S4, the flow path, the RO water chamber 42, the diluting chamber 43 (44) and the stirring chamber 46 are cleaned. Specifically, about 12 mL (about 6 mL to each diaphragm pump) of RO water flows into the diaphragm pump 45a (45b) with the negative pressure force by opening the electromagnetic valves 206, 208, and 213 (215) by the CPU 49a after the RO water newly produced in the RO water producing unit 7 is supplied to the RO water chamber 42. The electromagnetic valves 214 (216) and 209 are then opened with the electromagnetic valves 208 and 213 (215) closed, so that about 12 mL (about 6 mL to each diaphragm pump) of RO water in the diaphragm pump 45a (45b) is transferred to the diluting chamber 43 with the positive pressure force. The above operations are repeated 25 times to supply about 300 mL of newly produced RO water to the diluting chamber 43.

About 300 mL of RO water is then transferred from the diluting chamber 43 to the stirring chamber 46 by opening the electromagnetic valves 211 and 217 by the CPU 49a. The RO water in the stirring chamber 46 is discarded by opening the electromagnetic valves 218 and 221 with the electromagnetic valves 217 and 219 closed by the CPU 49a.

While the RO water is being transferred from the diluting chamber 43 to the stirring chamber 46, about 300 mL of newly produced RO water is supplied to the diluting chamber 44 through the operation similar to the operation of transferring to the diluting chamber 43. The transfer of the RO water from the diluting chamber 44 to the stirring chamber 46 is also performed through the operation similar to the operation of transferring from the diluting chamber 43 to the stirring chamber 46. Therefore, the interior of the flow path, the RO water chamber 42, the diluting chamber 43 (44), and the stirring chamber 46 are cleaned with the newly produced RO water through the series of operations described above. A predetermined amount of RO water is already stored in the RO water chamber 42 before step S3.

In step S5, the reagent is prepared in the stirring chamber 46 through the operation similar to the operation of preparing the reagent of desired concentration, and all prepared reagent are discarded. Specifically, after the reagent of the desired concentration is supplied to the stirring chamber 46 by the operations of steps S10 and S11, described later, the reagent in the stirring chamber 46 is discarded by opening the electromagnetic valves 218 and 221 with the electromagnetic valves 217 and 219 closed by the CPU 49a. Thus, even if the reagent having a concentration exceeding the desired concentration remains in the flow path, the diluting chamber 43 (44) and the stirring chamber 46, the reagent can be suppressed from being prepared to the concentration other than the desired concentration since cleaning is carried out with the reagent of the desired concentration in addition to the cleaning by the RO water.

The RO water is then supplied to the RO water chamber 42 in step S6. In step S7, whether or not a predetermined amount of high concentration reagent is accommodated in the high concentration reagent chamber 41 is determined based on the detection result of the float switch 100 by the CPU 49a. If the predetermined amount of high concentration reagent is not stored, the high concentration reagent is replenished to the high concentration reagent chamber 41 from the high concentration reagent tank 41a in step S8. Specifically, the electromagnetic valves 200 and 201 are opened with the electromagnetic valves 202 and 203 closed by the CPU 49a, so that the high concentration reagent is supplied to the high concentration reagent chamber 41 with the negative pressure force.

If the predetermined amount of high concentration reagent is accommodated in the high concentration reagent chamber 41, whether or not the predetermined amount of reagent is stored in the supply chamber 47 is determined by the CPU 49a. In other words, whether or not the reagent of greater than or equal to about 300 mL and less than or equal to about 600 mL is stored in the supply chamber 47 is determined. The process proceeds to step S16 if the predetermined amount of reagent is stored. If a predetermined amount of reagent is not stored, the electromagnetic valves 218 and 219 are opened, and the reagent is transferred from the stirring chamber 46 to the supply chamber 47 in step S10. In step S11, the electrical conductivity C is measured by the conductivity sensor 404 and the temperature T2 of the reagent is measured by the temperature sensor 405.

In step S12, whether or not the electrical conductivity C is within a predetermined range is determined by the CPU 49a. Specifically, whether or not the measured electrical conductivity C is within the predetermined range is determined with respect to the target value Z of the electrical conductivity at the diluting magnification of 25 times calculated by equation (2). If the electrical conductivity C is not within the predetermined range, the electromagnetic valve 219 is closed and the electromagnetic valve 221 is opened, and the reagent in which the electrical conductivity C is not within the predetermined range is discarded through the discard flow path in step S13. Only the reagent diluted at satisfactory accuracy thus can be stored in the supply chamber 47.

In step S14, the CPU 49a opens the electromagnetic valves 211 (212) and 217, and transfers the mixed solution in the diluting chamber 43 (44) to the stirring chamber 46 by negative pressure force. In this case, the transferred reagent is flowed along the inner wall of the stirring chamber 46 by the pipe 461 arranged in the stirring chamber 46 so as to be stirred in the stirring chamber 46. Thereafter, in step S15, the supply processing operation of the high concentration reagent and the RO water is executed instep S15.

The high concentration reagent and the RO water supply processing operation in step S15 of the reagent preparation processing operation shown in FIG. 10 will now be described with reference to FIGS. 6 and 11.

First, in the initial state (state immediately before reagent preparation process) of the reagent preparing device 6, the flow paths 301 to 304 shown in FIG. 6 are substantially filled with RO water and the flow path 300 is substantially filled with high concentration reagent.

Figure 11:
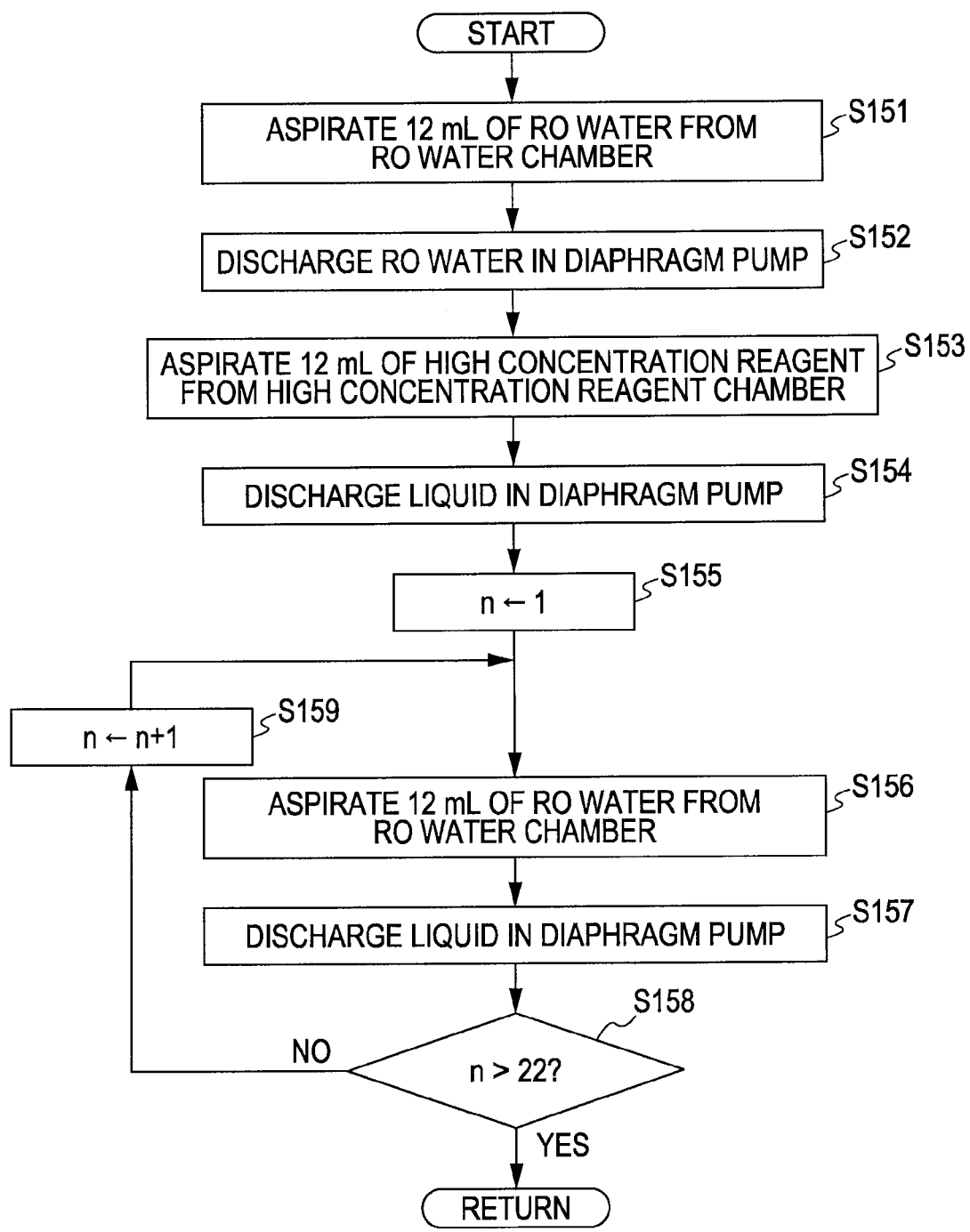
FIG. 11 is a flowchart explaining a supply processing operation of a high concentration reagent and RO water in step S15 of the reagent preparation processing operation shown in FIG. 10.

In step S151 of FIG. 11, about 12 mL (about 6 mL in each diaphragm pump) of RO water is aspirated from the RO water chamber 42 by the diaphragm pumps 45a and 45b. Specifically, the RO water flows to the diaphragm pump 45a (45b) by opening the electromagnetic valves 213 (215) and 208 by the CPU 49a. In step S152, the positive pressure is supplied to the diaphragm pump 45a (45b) by opening the electromagnetic valves 214 (216) and 209 after closing the electromagnetic valves 213 (215) and 208. Thus, about 12 mL (about 6 mL in each diaphragm pump) of RO water is supplied to the diluting chamber 43 through the flow paths 301 and 303.

Thereafter, in step S153, about 12 mL (about 6 mL in each diaphragm pump) of high concentration reagent is aspirated from the high concentration reagent chamber 41 by the diaphragm pumps 45a and 45b. Specifically, the negative pressure is supplied and the high concentration reagent is aspirated to the diaphragm pump 45a (45b) by opening the electromagnetic valves 202, 203, and 213 (215) after closing the electromagnetic valves 214 (216) and 209. Specifically, about 12 mL of high concentration reagent flowed out from the high concentration reagent chamber 41 mixes with the RO water remaining in the flow path 301, and the mixed solution of the RO water and the high concentration reagent is aspirated to the diaphragm pump 45a (45b). The mixed solution of the RO water and the high concentration reagent is filled in the flow path 301 in this case. In other words, about 12 mL of high concentration reagent flowed out from the high concentration reagent chamber 41 exists in a region combining the diaphragm pump 45a (45b) and the flow path 301 in this state. The high concentration reagent also exists in the flow path 300a, but can be substantially ignored as the amount of high concentration reagent existing in the flow path 300a is very small. Furthermore, at the time of aspirating the high concentration reagent after the second reagent preparation processing operation, the high concentration reagent remaining in the flow path 300a from the previous reagent preparation processing operation is pushed out to the flow path 301 side, and thus about 12 mL of high concentration reagent more accurately exists in the region combining the diaphragm pump 45a (45b) and the flow path 301.

In step S154, the positive pressure is supplied and the mixed solution of RO water and high concentration reagent is discharged from the diaphragm pump 45a (45b) by opening the electromagnetic valves 214 (216) and 209 after closing the electromagnetic valves 202, 203, and 213 (215). Thus, the mixed solution of RO water and high concentration reagent is supplied to the diluting chamber 43 through the flow paths 301 and 303. In this case, a few mL of high concentration reagent remains mixed with the RO water in the flow paths 301 and 303.

In step S155, n=1 is set by the CPU 49a. Here, n is the number of discharging of the RO water by the diaphragm pumps 45a and 45b, and is defined with a real number starting from 1. In step S156, about 12 mL of RO water is aspirated from the RO water chamber 42 by the diaphragm pumps 45a and 45b, similar to step S151. Similar to step S152, in step S157, the RO water is discharged from the diaphragm pumps 45a and 45b. Thus, the high concentration reagent remaining in the flow paths 301 and 303 is transferred to the diluting chamber 43 with the RO water.

Thereafter, in step S158, whether or not n is greater than 22 is determined by the CPU 49a. If n is not greater than 22, n=n+1 is set in step S159, and the operations of steps S156 to S159 are repeated until n is greater than 22. In other words, the operations of steps S156 to S159 are repeated until the aspiration and discharge operation of the RO water are performed 24 times with respect to one aspiration and discharge operation of the high concentration reagent by the diaphragm pumps 45a and 45b. The operation is terminated when n is greater than 22. Thus, about 12 mL×24 times=about 288 mL of RO water and about 12 mL×1 time=about 12 mL of high concentration reagent, that is, the mixed solution of about 288 mL+about 12 mL=about 300 mL is supplied to the diluting chamber 43. After the aspiration and discharge operation of the high concentration reagent by the diaphragm pumps 45a and 45b, the aspiration and discharge operation of the RO Water is performed 23 times, and thus the high concentration reagent remaining in the flow paths 301 and 303 are all transferred to the diluting chamber 43, and only the RO water consequently exists in the flow paths 301 and 303.

In the above operation, if the electromagnetic valve 210 is driven in place of the electromagnetic valve 209, about 300 mL of mixed solution containing about 288 mL of RO water and about 12 mL of high concentration reagent can be transferred to the diluting chamber 44.

Figure 10:
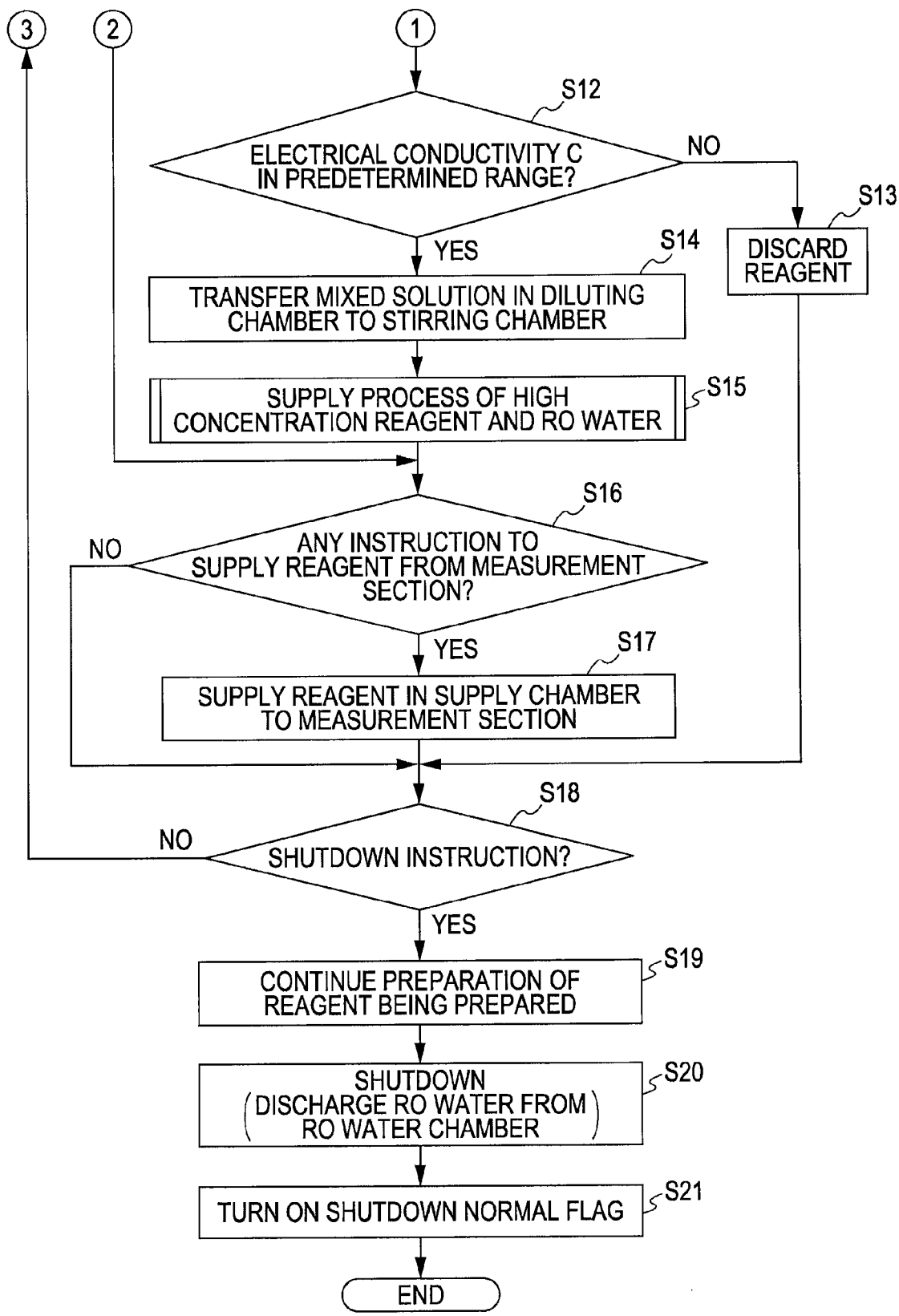
FIG. 10 is a flowchart explaining the reagent preparation processing operation of the reagent preparing device according to one embodiment of the present invention.

Whether or not an instruction to supply the reagent from the measurement section 2 transmitted through the data processing section 3 is made is determined by the CPU 49a in step S16 after the supply process of the high concentration reagent and the RO water is performed in step S15 of FIG. 10, and the process proceeds to step S18 if the instruction is not made. If the reagent supply instruction is made, the reagent in the supply chamber 47 is transferred to the measurement section 2 through the filter 471 by the negative pressure force supplied from the measurement section 2 in step S17. In step S18, the presence of shutdown instruction from the user is determined by the CPU 49a, and the process proceeds to step S6 if the instruction is not made.

If the shutdown instruction is made, the above operation is continued until the reagent in the middle of the preparation is ultimately transferred to the supply chamber 47 in step S19. Specifically, since the reagent preparation is continued by the operation of step S9 to step S15, the reagent diluted to a concentration different from the desired concentration remains in the flow path, the diluting chamber 43 (44), and the stirring chamber 46 if the operation is stopped in the middle of the preparation. Thus, the reagent diluted to a concentration different from the desired concentration is prevented from remaining in the flow path, the diluting chamber 43 (44), and the stirring chamber 46 by continuing the preparation operation in step S19.

In step S20, the shutdown is executed. In this case, the RO water is discharged from the RO water chamber 42. The RO water is thus prevented from being accumulated in the RO water chamber 42 until the reagent preparing device 4 is activated at the next time. Thereafter, in step S21, the flag indicating that the shutdown has been normally performed is set to ON, and the reagent preparation processing operation is terminated. The reagent preparation process shown in FIGS. 9 and 10, and the pneumatic unit operation start/stop processing operation shown in FIG. 12, described later, are continuously executed in parallel while the reagent preparing device 6 is operating by the CPU 49a.

Figure 12:
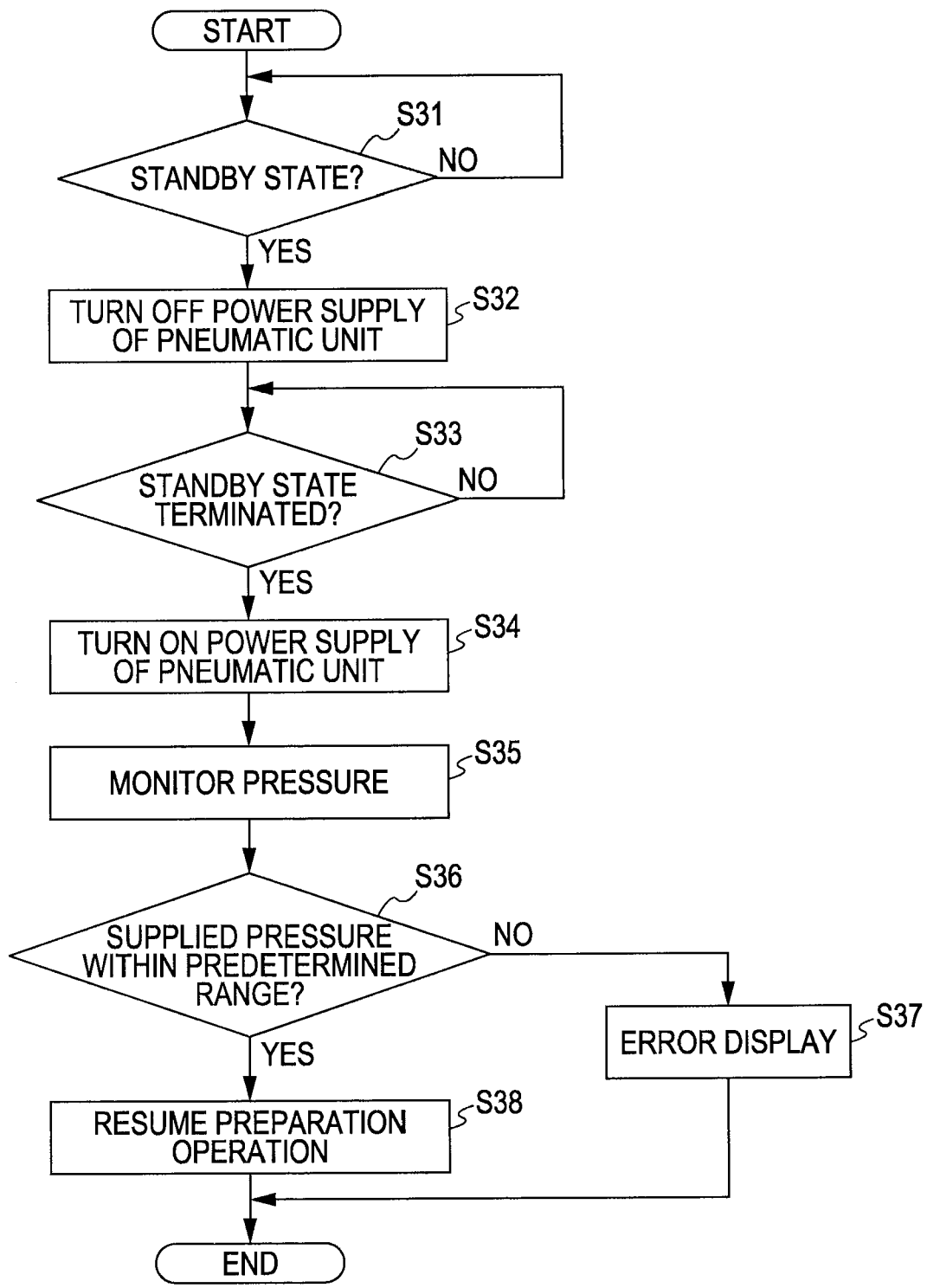
FIG. 12 is a flowchart describing the pneumatic unit operation start/stop processing operation of the reagent preparing device according to one embodiment of the present invention.

The pneumatic unit operation start/stop processing operation of the reagent preparing device 6 according to one embodiment of the present invention will now be described with reference to FIG. 12.

First, when the reagent preparing device 6 is activated, the reagent preparation processing operation shown in FIGS. 9 and 10 is executed, and the pneumatic unit 5 used in the transfer of the liquid enters the operating state. In other words, when the reagent preparing device 6 is activated, the motor 53 of the pneumatic unit 5 is driven, and the negative pressure force and the positive pressure force are generated by the negative pressure source 51 and the positive pressure source 52, respectively. In other words, when the reagent preparing device 6 is activated, the CPU 49a starts to supply the base current to the NPN bipolar transistor 50a of the pneumatic power supply control circuit 50. The CPU 49a determines whether or not the reagent preparing main body 4 is in the standby state, in which the reagent preparation operation is not executed, in step S31 in such state. Specifically, the CPU 49a determines that the reagent preparing main body 4 is in the standby state, in which the reagent preparation operation is not executed, if all six conditions are satisfied, (1) about 300 mL or more reagent is stored in the supply chamber 47, (2) the transfer of the reagent from the stirring chamber 46 to the supply chamber 47 (operation of step S10 of the reagent preparing process shown in FIG. 9) is terminated, (3) the transfer of the mixed solution from the diluting chamber 43 (44) to the stirring chamber 46 (operation of step S14 of the reagent preparing process shown in FIG. 9) is terminated, (4) the transfer of the high concentration reagent and the RO water to the diluting chamber 43 (44) (operation of step S15 of the reagent preparing process shown in FIG. 9) is terminated, (5) about 300 mL or more RO water is stored in the RO water chamber 42, and (6) about 300 mL of high concentration reagent is stored in the high concentration chamber 41.

Specifically, the CPU 49a detects that (1) about 300 mL or more reagent is stored in the supply chamber 47 based on the fact that the float portion of the float switch 106 of the supply chamber 47 is on the upper side than the lower limit position. The CPU 49a detects that (2) the transfer of the reagent from the stirring chamber 46 to the supply chamber 47 (operation of step S10 of the reagent preparing process shown in FIG. 9) is terminated based on the fact that the float portion of the float switch 105 of the stirring chamber 46 reached the lower limit position. The CPU 49a detects that (3) the transfer of the mixed solution from the diluting chamber 43 (44) to the stirring chamber 46 (operation of step S14 of the reagent preparing process shown in FIG. 9) is terminated based on the fact that the float portion of the float switch 103 (104) of the diluting chamber 43 (44) reached the lower limit position and the air bubbles are detected by the air bubble sensor 402 (403). The CPU 49a detects that (4) the transfer of the high concentration reagent and the RO water to the diluting chamber 43 (44) (operation of step S15 of the reagent preparing process shown in FIG. 9) is terminated based on the fact that the supply processing operation of the high concentration reagent and the RO water shown in FIG. 11 is terminated. The CPU 49a detects that (5) about 300 mL or more RO water is stored in the RO water chamber 42 based on the fact that the float portion of the flow switch 102 of the RO water chamber 42 is on the upper side than the lower limit position. The CPU 49a detects that 6) about 300 mL of high concentration reagent is stored in the high concentration chamber 41 based on the fact that the float portion of the flow switch 100 of the high concentration reagent chamber 41 is at the upper limit position.

The CPU 49a repeats the determination until the reagent preparing main body 4 is in standby, and turns OFF the power supply of the pneumatic unit 5 in step S32 when in standby. Specifically, the CPU 49a stops the supply of current to the coil 551 of the electromagnetic relay 55 of the pneumatic unit 5 by stopping the supply of base current to the NPN bipolar transistor 50a of the pneumatic power supply control circuit 50. The switch 552 is then returned and the electromagnetic relay 55 is in the non-conductive state (OFF state), and the supply of current to the motor 53 and the cooling fan 54 is stopped. As a result, the operation of the motor 53 and the cooling fan 54 is stopped, and the generating operation of the pressure by the positive pressure source 51 and the negative pressure source 52 is stopped.

Thereafter, in step S33, the CPU 49a determines whether or not the standby state is terminated, and repeats the determination until the standby state is terminated. Specifically, the CPU 49a determines that the standby state of the reagent preparing main body 4 is terminated when at least one of the six conditions (1) to (6) above is not satisfied.

When the standby state is terminated, the CPU 49a turns ON the power supply of the pneumatic unit 5 in step S34. Specifically, the CPU 49a resumes the supply of current to the coil 551 of the electromagnetic relay 55 of the pneumatic unit 5 by resuming the supply of base current to the NPN bipolar transistor 50a of the pneumatic power supply control circuit 50. The switch 552 is then moved and the electromagnetic relay 55 is in the conductive state (ON state). As a result, the supply of current to the motor 53 and the cooling fan 54 is resumed, and the operation of the motor 53 and the cooling fan 54 is resumed.

Thereafter, the CPU 49a performs pressure monitoring using the pressure sensors 400 and 401 in step S35. In step S36, the CPU 49a determines whether the magnitudes of the negative pressure force and the positive pressure force supplied from the pneumatic unit 5 to the reagent preparing main body 4 are within predetermined ranges, respectively, and displays on the display unit 48 an error display notifying that the pressure generated by the pneumatic unit 5 is abnormal in step S37 if not within the predetermined ranges. If the magnitudes of the negative pressure force and the positive pressure force are within the predetermined ranges, the CPU 49a resumes the reagent preparation operation in step S38. In other words, the CPU 49a resumes the liquid transfer operation using the negative pressure force and the positive pressure force supplied from the pneumatic unit 5.

In the present embodiment, the generation of pressure can be stopped and the power consumption of the pneumatic unit 5 can be reduced in the standby state in which the preparation operation is not executed by arranging the CPU 49a for determining whether or not in the standby state and controlling the generation of pressure by the pneumatic unit 5 according to the determination result. The power consumption of the reagent preparing device 6 thus can be reduced. Since the generating operation of the pressure by the pneumatic unit 5 can be stopped in the standby state, the lifespan of the negative pressure source 51 and the positive pressure source 52 including a piston pump, the motor 53, and the cooling fan 54 of the pneumatic unit 5 can be extended compared to when generating the pressure on a constant basis.

In the present embodiment, the CPU 49a is configured to determine that the reagent preparing main body 4 is in the standby state in which the reagent preparation operation is not executed when all six conditions, (1) about 300 mL or more reagent is stored in the supply chamber 47, (2) the transfer of the reagent from the stirring chamber 46 to the supply chamber 47 (operation of step S10 of the reagent preparing process shown in FIG. 9) is terminated, (3) the transfer of the mixed solution from the diluting chamber 43 (44) to the stirring chamber 46 (operation of step S14 of the reagent preparing process shown in FIG. 9) is terminated, (4) the transfer of the high concentration reagent and the RO water to the diluting chamber 43 (44) (operation of step S15 of the reagent preparing process shown in FIG. 9) is terminated, (5) about 300 mL or more RO water is stored in the RO water chamber 42, and (6) about 300 mL of high concentration reagent is stored in the high concentration chamber 41 are satisfied, so that the generating operation of the pressure by the pneumatic unit 5 can be stopped and the power consumption can be reduced when all six conditions (1) to (6) are satisfied.

In the present embodiment, the CPU 49a is configured to resume the generating operation of the pressure by the pneumatic unit 5 when the condition of at least (1) about 300 mL or more reagent is stored in the supply chamber 47 of the six conditions (1) to (6) is not satisfied after stopping the generating operation of the pressure by the pneumatic unit 5, so that the generating operation of the pressure is resumed and pressure of a predetermined magnitude is generated if about 300 mL or more reagent is not stored in the supply chamber 47 and there is a need to prepare a new reagent, and hence the state easily returns from the state of reducing power consumption to the state of newly preparing the reagent, and the preparation operation can be resumed.

In the present embodiment, the pressure sensor 400 (401) for detecting the magnitude of the pressure generated by the pneumatic unit 5 is arranged, and the CPU 49a is configured to resume the preparation operation when the magnitude of the generated pressure is within a predetermined range, so that the preparation operation can be resumed after confirming that the magnitude of the pressure increased to a predetermined magnitude, and the reagent preparation operation can be reliably resumed using the pressure of a predetermined magnitude generated by the pneumatic unit 5.

In the present embodiment, the pneumatic unit 5 includes the negative pressure source 51 and the positive pressure source 52 including the piston pump, the motor 53 for operating the piston, and the electromagnetic relay 55 for switching whether or not to supply the current to the motor 53, and the CPU 49a is configured to stop the generating operation of the pressure by controlling the switching operation between the conductive state (ON state) and the non-conductive state (OFF state) of the electromagnetic relay 55, so that the supply of current to the motor 53 can be easily stopped by simply switching the electromagnetic relay 55 between the conductive state (ON state) and the non-conductive state (OFF state), and the power consumption can be easily reduced in the standby state in which the preparation operation is not executed.

In the present embodiment, the CPU 49a is configured to stop the generating operation of the pressure in the standby state in which three reagent preparing main bodies 4 are connected to one pneumatic unit 5 and all of the three reagent preparing main bodies 4 are in the standby state where the preparation operation is not executed, so that the power consumption of the pneumatic unit 5 can be reduced even when a plurality of reagent preparing main bodies 4 are connected to one pneumatic unit 5.

In the present embodiment, each of the three reagent preparing main bodies 4 connected to one pneumatic unit 5 is configured to independently execute the preparation operation regardless of whether other reagent preparing main bodies 4 are executing the preparation operation, and the pneumatic unit 5 is configured so that the generating operation of the pressure is not stopped when at least one of the three reagent preparing main bodies 4 connected to one pneumatic unit 5 is executing the preparation operation, so that the CPU 49a of each reagent preparing main body 4 can independently and separately determine the execution state of the preparation operation, and the execution state of the preparation operation of each reagent preparing main body 4 can be easily determined. Thus, even when connecting a plurality of reagent preparing main bodies 4 to one pneumatic unit 5, the pneumatic unit 5 can be easily controlled based on the execution state of the reagent preparation operation of each reagent preparing main body 4.

The embodiments disclosed herein are illustrative in all aspects and should not be construed as being exclusive. The scope of the present invention is defined by the claims rather than by the description of the embodiments made above, and all modifications equivalent in meaning to the claims and within the scope of the claims are to be encompassed.

For instance, an example of a configuration of immediately turning OFF the power supply of the pneumatic unit when determined as the standby state has been described in the above-described embodiment, but the present invention is not limited thereto, and the power supply of the pneumatic unit may be turned OFF after elapse of a predetermined time after determined as the standby state.

An example of a configuration of continuously generating the pressure by the pneumatic unit serving as the pressure generator unit has been described in the above embodiment, but the present invention is not limited thereto, and the pressure may be intermittently generated by the pneumatic unit. In such a case, for instance, the pressure can be intermittently generated and a pressure of a predetermined magnitude can be supplied without continuously generating the pressure by again generating the pressure to increase the magnitude when the generated pressure is held in a sealed space having high air tightness, the held pressure is used in the reagent preparation operation, and the magnitude of the pressure becomes outside a predetermined range.

An example of a configuration of stopping the generating operation of the pressure by turning OFF the power supply of the pneumatic unit in the standby state has been described in the above embodiment, but the present invention is not limited thereto, and the magnitude of the generated pressure may be reduced by reducing the magnitude of the current to the motor serving as the drive source. In this case as well, the power consumption can be reduced by the amount the magnitude of the current to the motor is reduced. In the present specification, the stopping of the generating operation of the pressure is an example of reduction of the magnitude of the pressure.

An example of a configuration of resuming the generating operation of the pressure when the standby state is terminated has been described in the above embodiment, but the present invention is not limited thereto, and the generating operation of the pressure may be resumed based on the reagent supply request signal transmitted from the measurement section. In this case, the measurement section may transmit the reagent supply request signal when the measurement of the specimen started or may transmit the reagent supply request signal when aspirating the specimen.

An example of a configuration of stopping the generating operation of the pressure in the standby state has been described in the above embodiment, but the present invention is not limited thereto, and the generating operation of the pressure may be stopped in states other than the standby state as long as the reagent preparation operation is not being executed. As an example of a state other than the standby state, the generating operation of the pressure may be stopped in the local state for performing maintenance of the reagent preparing device. In this case, the generating operation of the pressure may be resumed only when a need to transfer the liquid by pressure arises during the maintenance.

An example of a configuration of connecting three reagent preparing sections to one pneumatic unit serving as the pressure generator unit has been described in the above embodiment, but the present invention is not limited thereto, and one reagent preparing section may be connected to one pressure generator unit, or a plurality of reagent preparing sections other than three may be connected to one pressure generator unit.

An example of a configuration of arranging a CPU serving as an execution determination means and a generation control means in each of the plurality of reagent preparing main bodies has been described in the above embodiment, but the present invention is not limited thereto, and only one CPU serving as the execution determination means and the generation control means may be arranged with respect to the plurality of reagent preparing main bodies. In this case, one CPU may determine the execution state of the preparation operation in all reagent preparing main bodies, and stop the generating operation of the pressure based on the determination result.

An example of a configuration of displaying an error display notifying that the pressure is abnormal on the display unit of the reagent preparing device has been described in the above embodiment, but the present invention is not limited thereto, and the display unit of the data processing section may display the error display notifying that the pressure is abnormal without arranging the display unit in the reagent preparing device.

An example of a configuration of arranging the pressure sensor serving as the pressure detection means in all flow paths connected to the negative pressure source and the positive pressure source has been described in the above embodiment, but the present invention is not limited thereto, and only two sensors, a pressure sensor for detecting the negative pressure force supplied from the negative pressure source and a pressure sensor for detecting the positive pressure force supplied from the positive pressure source, may be arranged, and the negative pressure force and the positive pressure force of after the detection may be distributed to each unit. The pressure sensor may be arranged in the pneumatic unit serving as the pressure generator unit.

An example of a configuration of arranging the RO water producing unit exterior to the reagent preparing device has been described in the above embodiment, but the present invention is not limited thereto, and the RO water producing unit may be arranged inside the reagent preparing device.

An example of a configuration of preparing the reagent from the high concentration reagent and the RO water in the reagent preparing device has been described in the above embodiment, but the present invention is not limited thereto, and the reagent may be prepared from a plurality of different types of liquids other than the high concentration reagent and the RO water in the reagent preparing device.

Figure 13:
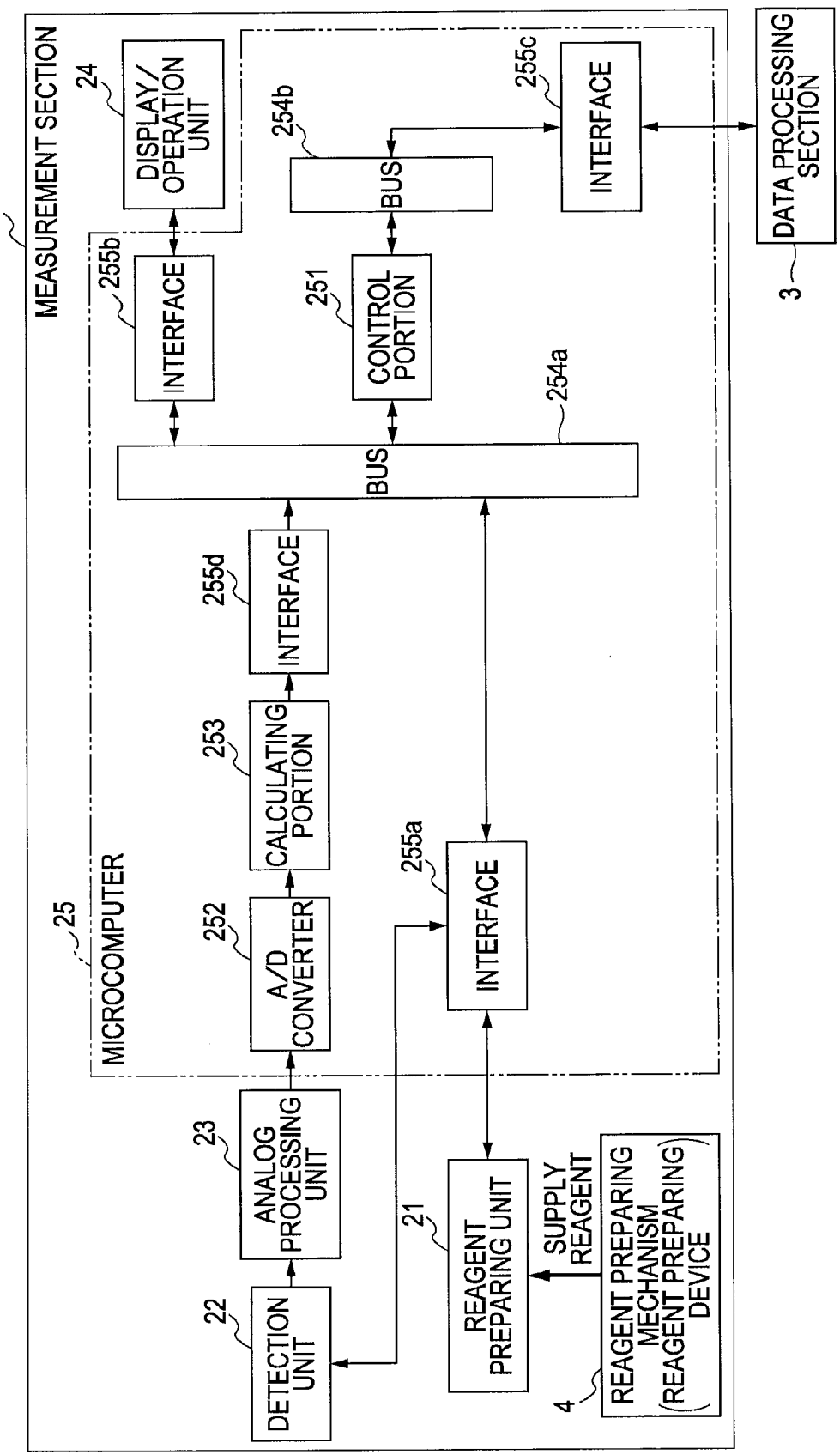
FIG. 13 is a block diagram describing a variant of the reagent preparing device according to one embodiment of the present invention.

In the above embodiment, the reagent preparing device installed separate from the measurement section has been described as one example of the reagent preparing device, but the present invention is not limited thereto, and it may be a reagent preparing device arranged in the measurement section and having a function of a reagent preparing mechanism, as shown in FIG. 13. The measurement section (device) equipped with the reagent preparing mechanism includes blood cell counting device, immune measurement device, and smear producing device.

What is claimed is:

1. A reagent preparing device capable of supplying a reagent, which includes a first liquid and a second liquid different from the first liquid, to a plurality of measurement apparatuses for measuring a specimen using the reagent, comprising:
    a pressure generator with a pressure generation mechanism which generates pressure to transfer liquid, and a switch device which switches to whether or not to supply current to a motor;
    a plurality of reagent preparing apparatuses, each respective reagent preparing apparatus is connected to the pressure generator to execute a preparation operation of the reagent using the pressure generated by the pressure generator, wherein each respective reagent preparing apparatus includes:
        a first vessel which accommodates the first liquid, which includes a first chamber and a first switch coupled to the first chamber and positioned for detecting whether or not a predetermined amount of the first liquid is accommodated in the first chamber;
        a second vessel which accommodates the second liquid, which includes a second chamber and a second switch coupled to the second chamber and positioned for detecting whether or not a predetermined amount of the second liquid is accommodated in the second chamber,
        a stirring chamber, connected to the first vessel and the second vessel through a flow path, configured to prepare the reagent using the first liquid and the second liquid, wherein the pressure generator is connected to the first-vessel, the second vessel and the stirring chamber;
        a supply chamber, connected to the stirring chamber, the supply chamber accommodates the reagent, and a third switch coupled to the supply chamber and positioned to detect whether or not a predetermined amount of the reagent is accommodated in the supply chamber; and
    a processor programmed to control the pressure generator to:

stop generation of the pressure by controlling the switching operation of the switch device in response to:
(i) a detection result that the first switch detects the predetermined amount of the first liquid in the first chamber for each and every one of the plurality of reagent preparing apparatuses,
(ii) a detection result that the second switch detects the predetermined amount of the second liquid in the second chamber for each and every one of the plurality of reagent preparing apparatuses, and
(iii) a detection result that the third switch detects the predetermined amount of the predetermined reagent in the supply chamber for each and every one of the plurality of reagent preparing apparatuses; and
continue generation of the pressure by controlling the switching operation of the switch device in response to at least one of:
(iv) a detection result that the first switch detects the predetermined amount of the first liquid is not in the first chamber for at least one of the plurality of reagent preparing apparatuses,
(v) a detection result that the second switch detects the predetermined amount of the second liquid is not in the second chamber for at least one of the plurality of reagent preparing apparatuses, and
(vi) a detection result that the third switch detects the predetermined amount of the predetermined reagent is not in the supply chamber for at least one of the plurality of reagent preparing apparatuses.

2. The reagent preparing device according to claim 1, wherein the processor is programmed to cause a determination that when transfer of liquid for preparing the reagent has been completed and to control the pressure generator to stop the generation of the pressure in response to a determination that transfer of liquid for preparing the reagent has been completed.

3. The reagent preparing device according to claim 2, wherein the processor is programmed to cause a determination that when transfer of the first liquid, the second liquid, and a mixed solution of the first liquid and the second liquid has been completed and to control the pressure generator to stop the generation of the pressure in response to a determination that transfer of the first liquid, the second liquid, and a mixed solution of the first liquid and the second liquid has been completed.

4. The reagent preparing device according to claim 1, wherein the processor is programmed to cause the pressure generator to control starting the generation of the pressure by starting a supply of the current to the motor in response to: (i) a detection result that the third switch detects the predetermined amount of the reagent is not in the supply chamber after the pressure generated by the pressure generator is stopped.

5. The reagent preparing device according to claim 4, wherein each respective reagent preparing apparatus further comprises a pressure sensor for detecting the magnitude of pressure generated by the pressure generator; and
the processor is programmed to resume the preparation operation by the respective reagent preparing apparatus in response to a detection result that the magnitude of the pressure detected by the pressure sensor reaches a predetermined range.

6. The reagent preparing device according to claim 1, wherein
the pressure generator further comprises a cooling fan connected to the switch device,
the switch unit switches whether or not to supply current to the cooling fan, and
the processor is programmed to stop the operation of the cooling fan by controlling the switching operation of the switch device.

7. A specimen processing system comprising:
a plurality of measurement apparatuses for measuring, each of which is configured to measure a specimen using a reagent which includes a first liquid and a second liquid which is different from the first liquid;
a pressure generator with a pressure generation mechanism which generates pressure to transfer liquid, and a switch device which switches to whether or not to supply current to a motor;
a plurality of reagent preparing apparatuses, each respective reagent preparing apparatus executes a preparation operation of the reagent using the pressure generated by the pressure generator, wherein each of the reagent preparing apparatus includes:
a first vessel which accommodates the first liquid, which includes a first chamber and a first switch coupled to the first chamber and positioned for detecting whether or not a predetermined amount of the first liquid is accommodated in the first chamber;
a second vessel which accommodates the second liquid, which includes a second chamber and a second switch coupled to the second chamber and position for detecting whether or not a predetermined amount of the second liquid is accommodated in the second chamber,
a stirring chamber, connected to the first vessel and the second-vessel through a flow path, configured to prepare the reagent using the first liquid and the second liquid, wherein the pressure generator is connected to the first vessel, the second vessel and the stirring chamber;
a supply chamber, connected to the stirring chamber and the measurement section, wherein the supply chamber includes a third switch coupled to the supply chamber and positioned for detecting whether or not a predetermined amount of the reagent is accommodated in the supply chamber; and
a processor programmed to control the pressure generator to:
stop generation of the pressure by stopping supply of current to the motor in response to:
(i) a detection result that the first switch detects the predetermined amount of the first liquid in the first chamber for each and every one of the plurality of reagent preparing apparatuses,
(ii) a detection result that the second switch detects the predetermined amount of the second liquid in the second chamber for each and every one of the plurality of reagent preparing apparatuses, and
(iii) a detection result that the third switch detects the predetermined amount of the reagent in the supply chamber for each and every one of the plurality of reagent preparing apparatuses; and
continue generation of the pressure by controlling the switching operation of the switch device in response to at least one of:
(iv) a detection result that the first switch detects the predetermined amount of the first liquid is not in the first chamber for at least one of the plurality of reagent preparing apparatuses, (v) a detection result that the second switch detects the predetermined amount of the second liquid is not in the second chamber for at least one of the plurality of reagent preparing apparatuses, and
(vi) a detection result that the third switch detects the predetermined amount of the predetermined reagent is not in the supply chamber for at least one of the plurality of reagent preparing apparatuses.

\* \* \* \* \*